(12) United States Patent
Holden et al.

(10) Patent No.: US 8,206,267 B2
(45) Date of Patent: Jun. 26, 2012

(54) VIRTUAL ANKLE AND BALANCE TRAINER SYSTEM

(75) Inventors: Maureen K. Holden, Waltham, MA (US); Constantinos Mavroidis, Arlington, MA (US); Ye Ding, Malden, MA (US); Joseph Malack, Rochester, NY (US); Rebecca Bularzik, North Andover, MA (US); Nathan Willard, Somerville, MA (US); Timothy Deso, Auburn, MA (US); Maciej Pietrusinski, Cambridge, MA (US); Brian Weinberg, San Diego, CA (US)

(73) Assignee: Northeastern University, Boston, MA (US)

( * ) Notice: Subject to any disclaimer, the term of this patent is extended or adjusted under 35 U.S.C. 154(b) by 8 days.

(21) Appl. No.: 12/960,837

(22) Filed: Dec. 6, 2010
(Under 37 CFR 1.47)

(65) Prior Publication Data
US 2011/0256983 A1     Oct. 20, 2011

Related U.S. Application Data

(60) Provisional application No. 61/266,591, filed on Dec. 4, 2009.

(51) Int. Cl.
*A63B 71/00* (2006.01)
(52) U.S. Cl. .................. 482/4; 482/34; 482/147
(58) Field of Classification Search .................. 482/1–9, 482/34, 79–80, 146, 147, 51; 434/247
See application file for complete search history.

(56) References Cited

U.S. PATENT DOCUMENTS

| | | | | |
|---|---|---|---|---|
| 6,152,854 | A | * | 11/2000 | Carmein ........................ 482/4 |
| 6,270,414 | B2 | * | 8/2001 | Roelofs ........................ 463/36 |
| 8,152,640 | B2 | * | 4/2012 | Shirakawa et al. ............ 463/36 |

* cited by examiner

*Primary Examiner* — Glenn Richman
(74) *Attorney, Agent, or Firm* — Weingarten, Schurgin, Gagnebin & Lebovici LLP

(57) ABSTRACT

A rehabilitation system that combines robotics and interactive gaming to facilitate performance of task-specific, repetitive exercise to enable individuals undergoing rehabilitation to improve the performance of coordinated movements of the ankle, and to practice balance activities, is disclosed. More specifically, the rehabilitation system includes at least one two degree-of-freedom robotic, haptic interface for a mammalian foot and interactive gaming hardware that is coupled to a controller, to provide a virtual reality-like environment.

22 Claims, 16 Drawing Sheets

VIRTUAL ANKLE AND BALANCE TRAINER SYSTEM

CROSS REFERENCE TO RELATED APPLICATIONS

This application claims the benefit of priority of U.S. Provisional Patent Application No. 61/266,591 filed on Dec. 4, 2009.

STATEMENT REGARDING FEDERALLY SPONSORED RESEARCH OR DEVELOPMENT

N/A

BACKGROUND OF THE INVENTION

1. Field of the Invention

A rehabilitation system that combines robotics and interactive gaming, i.e., visual interaction, to facilitate performance of task-specific, repetitive, ankle, balance and gait-related motor tasks, to enable individuals undergoing rehabilitation from neurological or orthopedic disorders to improve the performance of coordinated movements of the lower limb with special emphasis on the ankle muscles is disclosed. More specifically, the rehabilitation system includes a multiple degree-of-freedom (DOF), robotic ankle component, to assist users in improving or regaining function, strength, full range of motion, and motor control of their ankle(s), and balance trainer component, designed to assist users in retraining standing balance on a stable or moving surface, coordinating lower extremity control with specific ankle movements during uni- or bi-lateral standing activities such as static balance, weight shifting or stepping. Both components (ankle and balance trainer) interface with interactive gaming hardware that is coupled to a computer, to provide a virtual reality-like environment for movement practice.

2. Summary of the Prior Art

Stroke is the leading cause of disability in the United States with approximately 800,000 new cases reported annually, of which about 90,000 die. Typically, there are over 4.5 million stroke survivors in the population at any given time. The physical effects of stroke are variable and may include impairment in motor and sensory systems, language, perception, emotional and cognitive function. Impairment of motor function usually involves paralysis or paresis of the muscles on the side of the body that is contralateral to the side of the brain lesion.

For example, impaired control of gait and dynamic balance are frequent problems with stroke patients. Moreover, the ability to control ankle muscles and produce adequate range of motion in the ankle joints are key components of gait and balance function. Such deficits interfere with overall functional independence and can place patients at an increased risk for falls.

In a recent study of 972 stroke patients receiving in-patient rehabilitation in six facilities in the U.S., the most common treatment activity was gait-related activity. Indeed, more than 50 percent of these sessions involved work on balance and postural awareness. Pre-functional activities were the next most common treatment, and greater than 50 percent of these sessions involved strength training.

The importance of balance control with respect to gait function has been shown in a recent study. The study concluded that balance control is more important in improving walking ability than are improvements in leg strength or muscle synergy control. Other authors have shown that deficits in mobility, muscle strength, and motor control about the ankle joint are key factors that contribute to gait and balance deficits in stroke patients. Although this disclosure will discuss use of the invention by a stroke patient, the invention is applicable to any patient suffering from neurological disorders, including traumatic brain injury (TBI), multiple sclerosis, and Parkinson's disease, or needing to rehabilitate ankle muscles, for example, as a result of orthopedic or sports-related injuries.

Presently, there are no commercially-available devices that are designed for ankle rehabilitation that combine the ability to train balance function, ankle strength, mobility, and motor control into one system, nor do any of the commercially-available devices typically allow use of the device in multiple positions, i.e., standing, sitting, and positions in between. Examples of currently-available devices used for ankle rehabilitation include Wobble Boards, the Ankle Foot Orthosis at University of Delaware (AFOUD), a Robotic Gait Trainer (RGT), a Powered Ankle-Foot Orthosis (PAFO), an Ankle Dorsiflexion/Plantarflexion Exercise Device (ADPED), and the Rutgers Ankle (RA).

Wobble Boards are low cost wooden or plastic platforms to which a rubber semi-sphere is attached to the bottom of the board. Users stand on the board and attempt to balance themselves. Although Wobble boards can be useful for balance training, they are often too difficult for stroke patients to use safely. Furthermore, they do not provide quantitative measurement output that could be used to adjust exercise difficulty and/or to measure patient progress over time.

The AFOUD is a two degree-of-freedom (DOF) ankle device having three links that are connected by two revolute joints corresponding to the three links. The AFOUD can be used as a stand-alone measurement device to measure joint forces and moments applied at both ankle joints.

The RGT, PAFO, and ADPED are devices to assist stroke patients. The RGT is a tripod mechanism that includes a flat plate and two bi-directional actuators that are controlled by a Matlab and Simulink platform. The RGT, however, does not provide a quick response time and its weight and bulkiness do not promote easy wear by stroke patients. The PAFO includes a carbon fiber and polypropylene shell that is wrapped around a patient's leg. A steel hinge joint couples a footplate to the shell. Two artificial pneumatic muscles are controlled by proportional myoelectric control. This robotic exoskeleton device could provide plantarflexion/dorsiflexion (PF/DF) torque at the ankle, but lacks inversion/eversion movement control. The ADPED is another passive motion exercise device for PF/DF movement. However, patients are limited to using this device in a seated position. Furthermore, the RGT, PAFO, and ADPED are designed to provide passive robotic assistance instead of active movement control. They also do not address the balance component of training or comprehensive training of ankle motion and strength control in all planes of movement. Finally, they do not offer an interactive, virtual reality-based (VR-based) interface.

The Rutgers Ankle (RA) incorporates a Stewart platform having six pneumatic pistons working in parallel to create a six-DOF platform. In use, the RA is interfaced with VR software that guides the user's movements and controls the force feedback of the platform. Disadvantageously, the RA can only be operated in a seated position where the thighs are at a 90-degree angle to the torso and the knees are bent at a 90-degree angle. It does not provide balance control training. In addition, it is not commercially available, and would likely be expensive to produce due to its use of expensive sensors and actuators.

The Balance Master was purportedly developed to provide objective assessment and retraining of sensory and voluntary motor control of balance with visual biofeedback. The Balance Master utilizes a fixed, dual-force plate on which a patient stands, to measure the vertical forces exerted by the patient's feet. The center of pressure (COP) of these forces can then be calculated, and used to measure weight shifting and body sway. This is primarily a training device. Another more expensive device produced by the same company, the NEUROCOM uses a force plate that can also be moved (linear translation or angular rotation in the anterior-posterior direction), as well as a visual surround that can be coupled to the force plate movements. This system is designed primarily for diagnosis, especially of vestibular-related balance disorders. The interactive technology and clinically proven protocols allow a clinician/practitioner to objectively and systematically assess sensory and voluntary motor components of balance control.

SUMMARY OF THE INVENTION

A virtual ankle and balance trainer (VABAT) system is disclosed. The primary function of the VABAT system is to assist neurological patients to retrain normal motor control of the ankle through traditional strength and ROM exercises, but also to allow more sophisticated training of coordination such as improving reciprocal motion control and speed, increase the ability to rapidly generate torque in various directions, coordinate ankle dorsiflexion or plantarflexion with various degrees of hip and knee extension. Very weak patients would begin training in sitting but could progress to a more extended leg position and eventually to a standing position for training. A key and unique feature of the device is to use it as an ankle robotic device that is adapted to actively assist movement a user's foot or feet. Through software controllers, one could mimic the assistance provided by a skilled therapist, where the patient's movements are resisted in the part of the range where they are strong and assisted in the parts of the range where they are weak. A VR interface can be used to provide patients with salient feedback about their performance to facilitate and speed up motor learning.

The second function of the VABAT system is to help neurological patients train their balance function through repeated practice in shifting their center-of-pressure (COP) with their foot or feet in a myriad of configurations. Early training would use a stable platform, while more advanced training would use a moving platform under robotic control. The 'moving mode' could be used to simulate in VR functional situations in the real world for balance training, such as walking on uneven surfaces, or recovering the balance after stepping in a small hole. More particularly, the VABAT system is capable of providing variable torque resistance during plantarflexion/dorsiflexion (PF/DF) and/or inversion/eversion, as well as combined motions of circumduction; of measuring the force on the footplate; of calculating the COP or the user's foot; of being used in standing and seated positions; and of visually displaying interactive, virtual reality programs to the patient for ankle and balance training. Advantageously, the VABAT can be used as an ankle kinematic measurement device, which can be fabricated at low cost. Kinetic measures can also be derived to measure progress. Uses of the device can include, for the purpose of illustration and not limitation, entertainment and athletic training. The device can also be used as an ankle robotic device that is adapted to actively move a user's foot or feet.

BRIEF DESCRIPTION OF THE DRAWINGS

The invention is pointed out with particularity in the appended claims. The advantages of the invention described above, together with further advantages, may be better understood by referring to the following description taken in conjunction with the accompanying drawings. The drawings are not necessarily drawn to scale, and like reference numerals refer to the same parts throughout the different views.

DESCRIPTION OF THE INVENTION AND ITS PREFERRED EMBODIMENTS

Figure 1A:
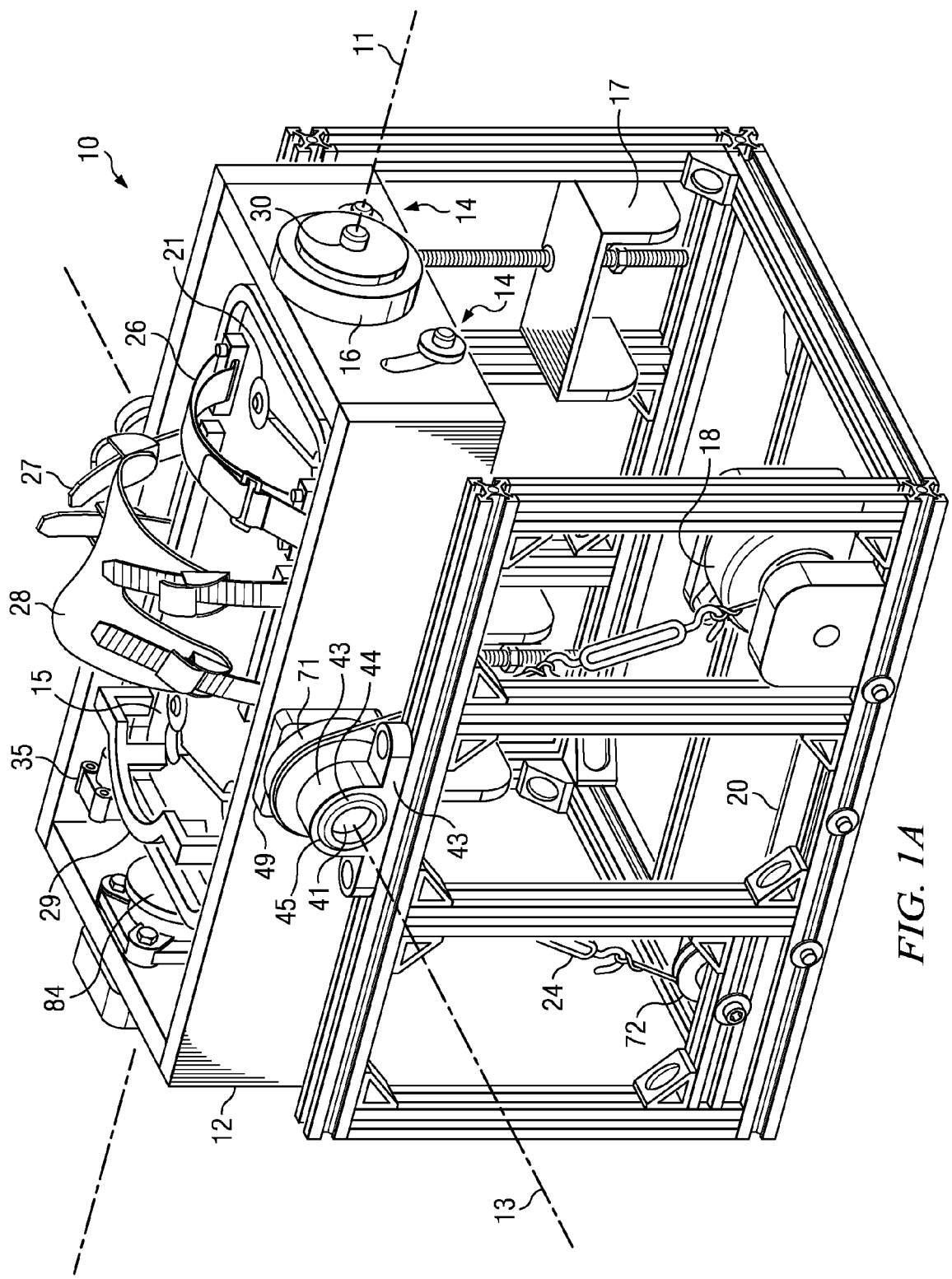
FIG. 1A shows a diagrammatic view of a first embodiment of a robotic haptic interface with dampers in accordance with the present invention.

The mechatronic, virtual ankle and balance trainer system disclosed herein includes hardware and software components, which are described in greater detail below. The hardware components of the VABAT rehabilitation system include a stable, stationary platform, a controllable, selectively-movable, multiple degree-of-freedom (DOF) robotic platform that is adapted to be coupled to a user's foot and ankle; a gaming interface; and a computer-based controller with a data acquisition system.

A multiple degree-of-freedom ankle rehabilitation system was described in U.S. Provisional Patent Application No. 61/266,591 filed on Dec. 4, 2009, which is incorporated herein in its entirety by reference. Although this disclosure will describe the VABAT system and computer interface in terms of only two degrees-of-freedom, those of ordinary skill in the art can appreciate that a more sophisticated system with additional degrees-of-freedom, i.e., greater than two, can be made in accordance with the teachings of this disclosure.

The virtual ankle and balance trainer system (VABAT) disclosed herein has two modes of operation, viz., a stable mode and a dynamic mode, and can be used in a sitting position, a standing position or some position in between the two. Used in the stable mode, in the standing position, the system can be used as a force platform, monitoring forces exerted by a user's single foot or both of the user's feet on the force plate, for determining force distribution and center-of-pressure (COP). In the sitting position, forces applied by the user are measured by a robotic, haptic interface. This mode can be used to measure or train isometric strength in a variety of fixed positions. Used in the dynamic mode, the robotic, haptic interface is structured and arranged to move in at least two-degrees of freedom, e.g., pitch and roll, enabling ankle motion and ankle strengthening exercises.

In a sitting position and dynamic mode of operation ("sitting-dynamic"), patients (hereinafter referred to as "users" to include individuals who use the device or system for other than medical rehabilitation purposes) can produce "pitch" angular rotation that is orthogonal to the plane of the sole of the foot, viz., plantarflexion and/or dorsiflexion (PF/DF) or "roll" angular rotation, viz. inversion and/or eversion, which are important components of ankle control. In a sitting-stable mode, it is important to note that the forces applied to the footplate would yield inaccurate COP measures due to the angle or trajectory of the foot relative to the supporting platform. Thus, in this position, force data is derived from the MRF motor settings. The sitting-stable mode is ideal for isometric sitting exercises, while the moving mode in sitting will enable dynamic ankle motion and ankle strengthening exercises.

In a standing position and stable mode of operation ("standing-stable"), users can learn to maintain their balance using COP and/or center of gravity data. For example, while in the standing position, as a user begins to lose his/her balance, he/she learns to shift his/her weight or foot position to regain or maintain his/her balance and/or to quickly and safely remove his/her foot from the robotic, haptic interface onto the surrounding stable, supporting platform. A unique aspect of this system is the ability to monitor COP of each foot individually, one at a time or the two can be combined in software for a traditional 2-foot COP measure. In a standing-dynamic mode, the system can be used to actively provide for different foot trajectories to simulate uneven terrain for more advanced users.

Figure 1B:
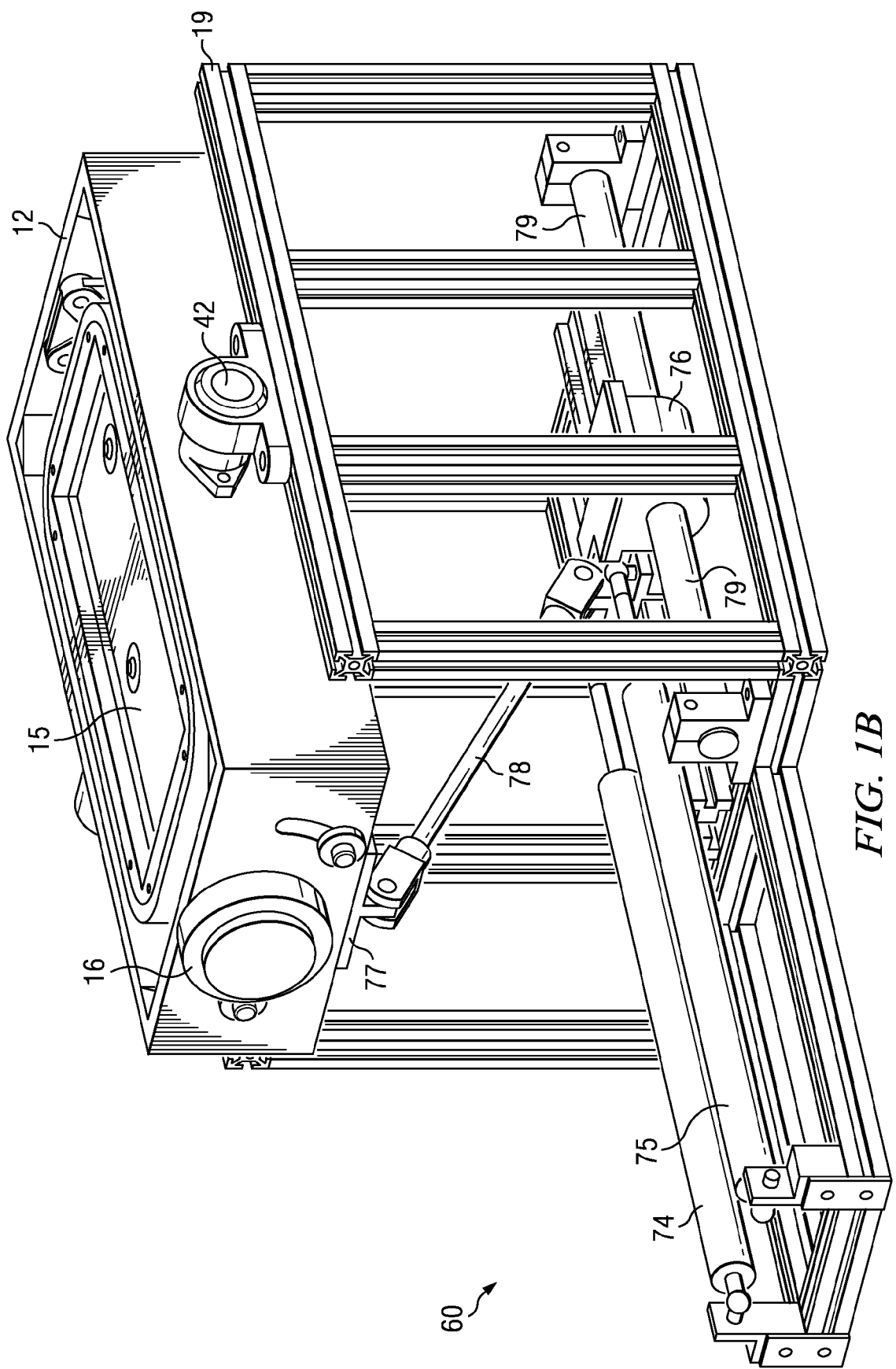
FIG. 1B shows a diagrammatic view of a second embodiment of a robotic haptic interface in accordance with the present invention.

A key element of the VABAT system is the robotic, haptic interface that is releasably attachable to a user's foot for ankle motion and ankle strengthening exercises. This is used only in dynamic mode. Referring to FIG. 1A and FIG. 1B, various embodiments of a robotic, haptic interface of the VABAT systems are shown. The haptic interface shown in FIG. 1A will be described in greater detail first and then those portions that differ between the FIG. 1A and the FIG. 1B embodiments will be described.

Figure 3:
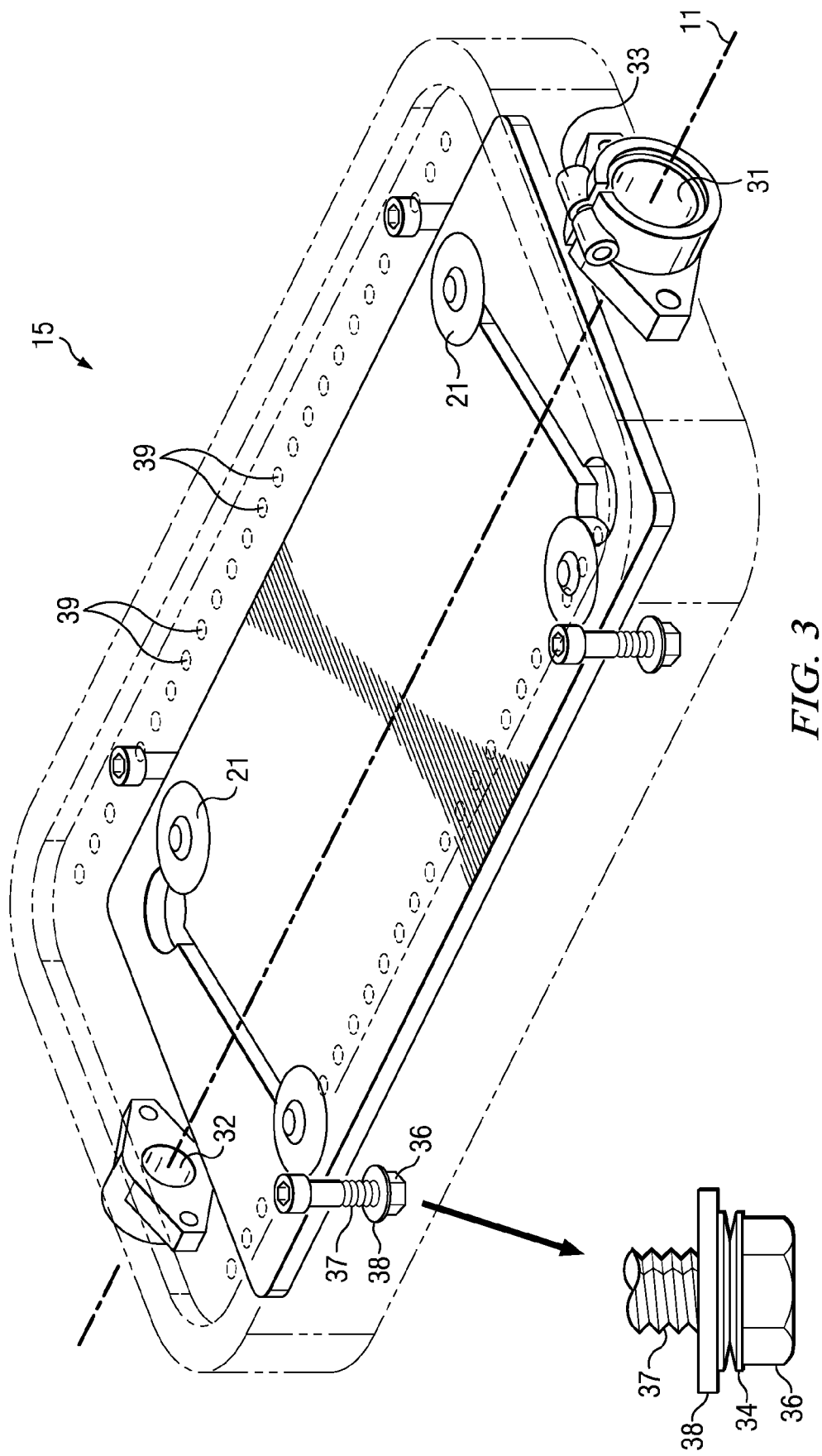
FIG. 3 shows a diagrammatic isometric view of a footplate for the haptic interface of FIG. 1A and FIG. 1B.

The haptic interface is a relatively-small, two-degree-of-freedom (2-DOF) device 10 that includes a moveable platform ("footplate") 15 that is housed within a box portion 12 that is supported by a support structure 19. As shown in FIG. 3, the smaller footplate 15, e.g., a 14 inch by 7 inch by 0.375 inch aluminium plate, is structured and arranged to move about an anterior-posterior axis 11 to enable inversion/eversion or roll movements about the anterior-posterior axis 11. A pair of openings 31, 32 are provided to accommodate the anterior-posterior shaft 30. A clamping means 33 can be provide at one or both openings 31, 32 to releasably attach the footplate 15 to the shaft 30 so that any roll movement of the footplate 15 will cause an identical or virtually identical rotation of the shaft 30.

To measure the foot force exerted on the footplate 15 for the purpose of calculating force distribution, COP, and the like, a plurality of load cells 21 are integrated into the footplate 15. The load cells 21, e.g., Model 53-CR load cells with a 5 to 500 pound range manufactured by Honeywell, provide pressure sensing data at the discrete locations for calculating the COP of the forces that are applied normal to the footplate 15. Although FIG. 3 shows four load cells 21 shown in the each of the four corners of the footplate 15, this is done for illustrative purposes only. There could be more or fewer load cells 21 used and the disposition of the load cells 21 does not have to be in the four corners of the footplate 15. For example, one or two load cells could be disposed where the ball of a user's foot might be placed and one or two load cells could be disposed when the heel of the user's foot might be placed.

Because the operating and measuring range of the load cells 21 does not start at zero, a pre-load is desirable, especially to realize small force measurements and to maintain precision measurements. For that purpose, disc springs 34 can be inserted between a washer 38 and fastening device 36, i.e., nut, on fastening bolts 37.

The footplate 15 includes a heel cup 29 and a plurality of tapped holes 39 on both sides of the aluminium portion. The heel cup 29 is disposed at the posterior end of the footplate 15 to accommodate the user's heel and, moreover, to ensure that the heel of a user's foot starts from a common position each time. The heel cup 29 can be manufactured from rapid-prototyping material or from a padded metal, for example.

Figure 4:
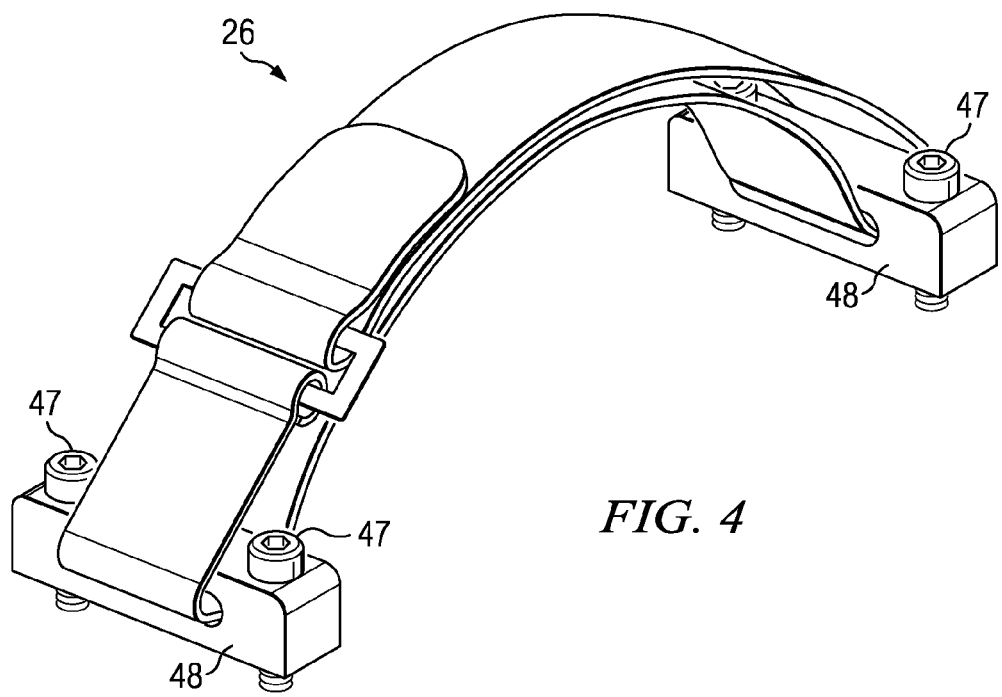
FIG. 4 shows a diagrammatic view of a toe binding.

The tapped holes 39 are structured and arranged for releasably attaching foot binding covers 27 and 28 and a toe binding strap 26 to the footplate 15. FIG. 4 shows a representative toe binding strap 26. The foot binding covers 27 and 28 and is necessary to allow users to train dorsiflexion movements with resistance. Advantageously, the bindings 27 and 28 and physical disposition of the bindings 27 on the footplate 15 are adjustable to better fit different sizes, viz. widths and lengths, of feet.

The foot binding covers 27 and 28 and the toe binding strap can be off-the-shelf products, which include a mounting device 48 and a plurality of fastening devices 47. The mounting device 48 is structured and arranged to be releasably attached to the footplate 15 using the fastening devices 47 and corresponding tapped holes 39. Although not shown in FIG. 4, similar mounting devices and fastening devices can be used to releasably attach the foot binding covers 27 and 28 to the footplate 15.

Referring again to FIG. 1A, the box portion 12 is structured and arranged to accommodate the footplate 15 and anterior-posterior shaft 30 and to rotate about a pair of cylindrical rods ("PF/DF shafts") 41, 42. The PF/DF shafts 41, 42 are fixedly attached to the outer surface and on opposing sides of the box portion 12 using a mounting device 49, to provide a lateral-medial axis 13 of rotation. The PF/DF shafts 41, 42 are rotatable attached to the support structure 19 within a hole 45 through a mounting bracket 43. A frictionless or substantially frictionless bearing 44 is disposed between the PF/DF shafts 41, 42 and the surface of the hole 45, to allow the PF/DF shafts 41, 42 to rotate freely about the lateral-medial axis 13. Although the location of the PF/DF shafts 41, 42 and mounting bracket 43 shown in FIG. 1A is shown roughly at the midpoint of the box portion 12, more preferably, the PF/DF shafts 41, 42 and mounting bracket 43 would be disposed closer to axis of the user's ankle joint and aligned with the medial and lateral malleoli, to accommodate all possible ankle pitch motions during PF/DF rotation. Users can also perform circumduction by simultaneously moving about the anterior-posterior 11 and lateral-medial axes 13.

Figure 5:
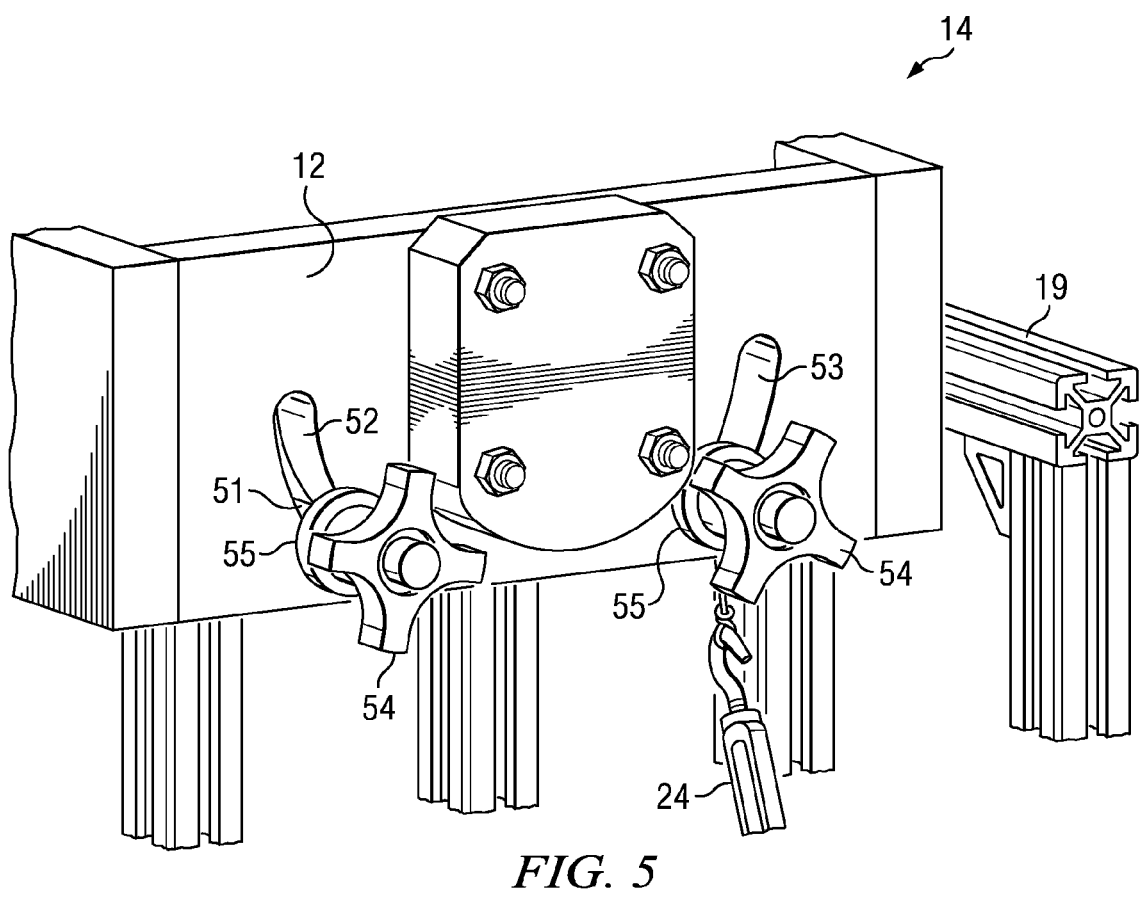
FIG. 5 shows a diagrammatic view of a first mechanical stop for the haptic interface shown in FIG. 1A and FIG. 1B for limiting inversion and eversion movement.

The haptic interface 10 includes adjustable mechanical stops 14, 17 and controllable actuators 68 (FIG. 1D), dampers and/or brakes 16, 18 to enhance ankle mobility and strength training. Adjustable mechanical stops 14, 17 are provided to allow a clinician or practitioner to alter or control the range of motion of the haptic interface 10 in PF/DF and/or in inversion/eversion, to suit the needs and capabilities of a discrete user. For example, for controlling inversion/eversion motion limits, referring to FIG. 5, a first mechanical stop 14 can include a pair of aluminium rods 51 that are in parallel or substantially in parallel with the anterior-posterior shaft 30. The aluminium rods 51 are disposed through the box portion 12 via pairs of curved slots 52, 53, which are provided in opposing, distal and proximal ends of the box portion 12. The distal ends (not shown) of each of the aluminium rods 51 include an anchoring means that is greater in an outer dimension than the smallest dimension, e.g., width, of the curved slots 52, 53 to prevent the rods 51 from moving into the box portion 12.

At proximal ends of the aluminium rods 51, rotating, tightening knobs 54 and pads 55, e.g., a rubber, silicon or plastic pads, which are greater in outer dimensions than the smallest dimension of the curved slots 52, 53, e.g., width, are provided. The knobs 54 are adapted to tighten the corresponding pads 55 against the box portion 12, to hold the aluminium rods at a desired position (elevation) by friction and or compressive forces. Positioning the aluminium rods 51 at the bottommost portion of the curved slots 52, 53 allows the greatest range of motion in inversion/eversion. Positioning the aluminium rods 51 at the uppermost portion of the curved slots 52, 53 allows the least range of motion in inversion/eversion. Those of ordinary skill in the art can appreciate that the aluminium rods 51 can be positioned at different elevations, for example, to permit a greater range in inversion than in eversion, or vice versa. Although the rods 51 are described as being made of aluminium, any suitable rigid material can be used.

Figure 6:
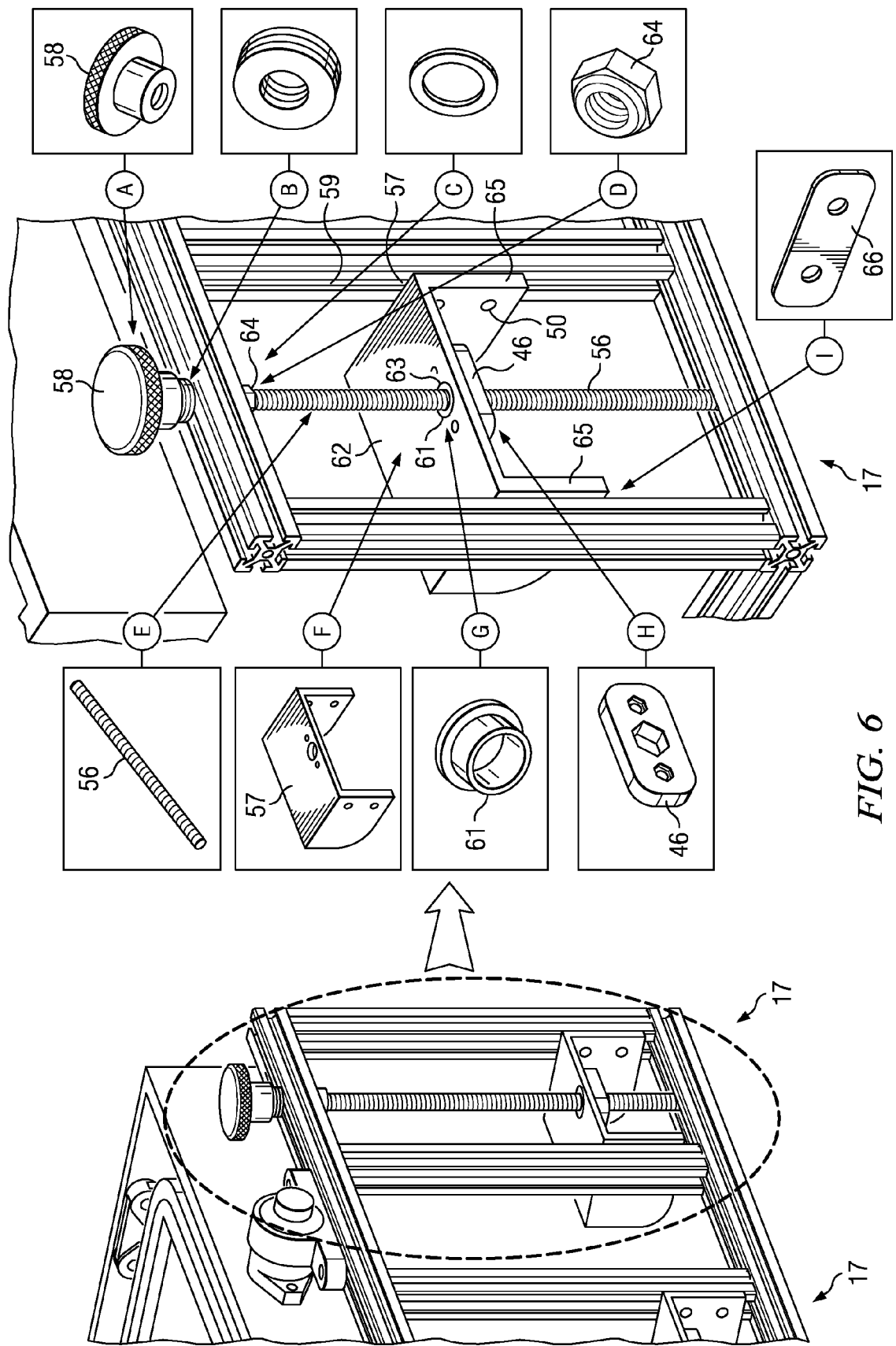
FIG. 6 shows a diagrammatic view of a second mechanical stop for the haptic interface shown in FIG. 1A and FIG. 1B for limiting plantarflexion and dorsiflexion motion.

To control the range of PF/DF motion, a pair of adjustable second mechanical stops 17 are provided on and movably attached to the support structure 19. The second mechanical stops 17 are disposed on either side of the mounting bracket 43, to alter and/or control PF/DF rotation, to prevent overstretching, or to allow training in motor control in a specific range of motion that is needed by a particular user. Exemplary second mechanical stops 17 are shown in FIG. 6.

Each of the exemplary second mechanical stops 17 includes a vertical or near vertical lead screw 56 that is held in said position using a knob 58 atop a thrust bearing and a locking nut 64 at a first end of the lead screw 56. The second end of the lead screw doe not have to be attached and can be floating. The lead screw 56 is disposed through a C-channel, "holding block" 57, via a friction sleeve 61 in a hole 63 in an upper, planar portion 62 of the holding block 57.

A selectively translatable positioning device 46 that also fits on the lead screw 56 can be positioned on or at the bottom face of the planar portion 62 to retain the holding block 57 at a desired elevation. To minimize or prevent further rotation when force is applied to it, the holding block 57 is also provided with a hole(s) 50 on each of the legs 65 of the C-channel 57 through which a corresponding pin(s) (not shown) can be inserted. The pin(s) is/are structured and arranged so that their distal ends fit into a vertical track 59 in the support structure 19. Accordingly, when load is applied to the planar portion 62 of the holding block 57, rotation is minimized or prevented by transferring loads from the positioning device 46 to the lead screw 56 and by transferring loads from the distal ends of the pins to the walls of the vertical track 59.

The planar portion 62 of the holding block 57 for each of the second mechanical stops 17 can be selectively positioned at any elevation. Moreover, the elevation of the plantarflexion motion holding block 57 can be set differently that the elevation of the dorsiflexion motion holding block 57 to allow greater range of motion in plantarflexion than dorsiflexion, or vice versa.

Hydraulic actuators, dampers, brakes, and the like, are provided to allow a controllable variable resistance and/or torque generation in the shaft 30 along the anterior-posterior axis 11 and/or shafts 41 along the lateral-medial axis 13. Whereas dampers and brakes 16, 18 are structured and arranged to provide passive resistance to an applied force, actuators 68 (FIG. 1D) are also adapted to produce active movement, which is to say a full robotic capability. Dampers 16, 18 can be any controllable mechanical dampers, which can include magneto-rheological fluid (MRF) dampers. Actuators 68 can include electro-rheological fluid (ERF) actuators. Although, the invention will henceforth be described as having MRF dampers, this is only done for illustrative purpose.

In operation, MRF dampers 16, 18 are adapted to control the torque output about the shaft 30 along the anterior-posterior axis 11 and about the shaft 41 along the lateral-medial axis 13 by adjusting the intensity of a magnetic field, which alters the characteristics of the magneto-rheological fluid in the damper 16, 18, making it more resistive when there is a stronger field or less resistive when there is a weaker field. The adjustable magnetic field is controlled by the input current. Hence, practitioners and/or clinicians can adjust the exercise difficulty by providing more or less current to the dampers 16, to vary the resistance of each 16, 18. This also enables practitioners to quantitatively measure the user's performance.

Figure 7:
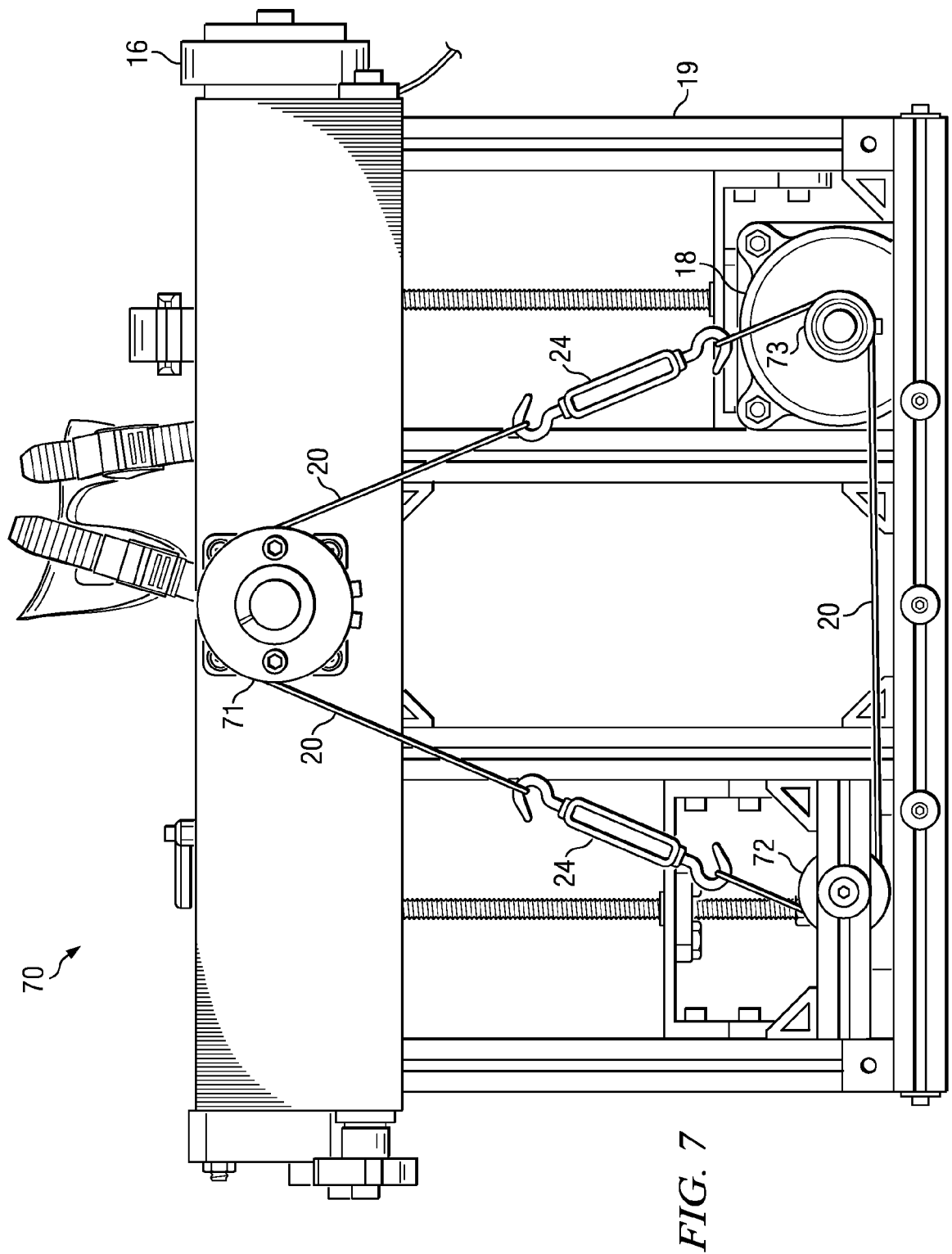
FIG. 7 shows a diagrammatic side view of a cable-drive torque amplification mechanism for the haptic interface shown in FIG. 1A and FIG. 1B.

The output torque of the MRF dampers 16 can range from 0.25-6 Nm during inversion/eversion rotation, which is a proper resistance range for patients with stroke. However, the strength of the muscles which controls inversion/eversion, is weaker than the muscles used for PF/DF movements (e.g., normal strength plantarflexors can easily lift the body weight repeatedly). As a result, the PF/DF resistance torque needs to be amplified for anterior-posterior movements. To that end, an exemplary cable drive torque amplification mechanism 70 is shown in FIG. 7. Other amplification mechanisms can include timing belts, gearboxes, piston dampers (FIG. 1B), and the like.

The amplification mechanism 70 can include a large pulley 71 and two small, round gears 72, 73. The large pulley 71 can be fixedly attached to the PF/DF shaft 41 so that rotation of the PF/DF shaft 41 causes a proportional rotation of the pulley 71. One of the round gears 72 is rotatably attached to the support structure 19. The other round gear 73 is mechanically coupled to the MRF damper 18. A steel wire 20 can be routed around the two round gears 72, 73 and the ends of the steel wire 20 can be fixedly attached to the steel pulley 71, e.g., using set screws disposed thereon. Turn buckles 24 can be disposed between the round gears 72 and 73 and the steel pulley 71, to tighten the steel wire 20 to provide sufficient friction to drive the gear 73 that is coupled to the MRF damper 18. Keeping the steel wire 20 taut, prevents or minimizes backlash during anterior-posterior movements, viz. PF/DF.

As the user applies force to the footplate 15 to cause PF/DF rotation, the steel pulley 71 rotates, causing the steel wire 20 to transmit torque from the gear 73 to the damper 18. The ratio of the gear on the brake shaft 73 to the gear on the steel pulley 71 is 1:2.5 in the illustrated embodiment. Thus, the resistance torque is amplified by 2.5 times, and the range of the torque of the PF/DF would be from 0.25-15 Nm. Those of ordinary skill in the art can appreciate that the amplification works when the device is used passively in response to user applied loads or actively to effect movement of the user's foot using the damper.

Alternatively, in lieu of using a second MRF damper 18 for anterior-posterior movement, a controllable piston damper system 60 can be used. Referring to FIG. 1B, the piston damper system 60 can include a plurality of adjustable piston dampers 74, 75, linear bearings 79 that are arranged in parallel or substantially in parallel with the axes of the piston dampers 74, 75, and a clevis arm 78 that is mechanically coupled to the pistons dampers 74, 75 and to a movable block 76 that is disposed on the linear bearings 79. The clevis arm 78 is rotatable attached to a mounting device 77 that is disposed at the posterior end of the underside of the box portion 19. In operation, plantarflexion rotation causes the clevis arm 78 to move towards the anterior end of the box portion 19, pulling the piston dampers 74, 75. Dorsiflexion rotation causes the clevis arm 78 to move towards the posterior end of the box portion 19, compressing the piston dampers 74, 75.

Figure 1C:
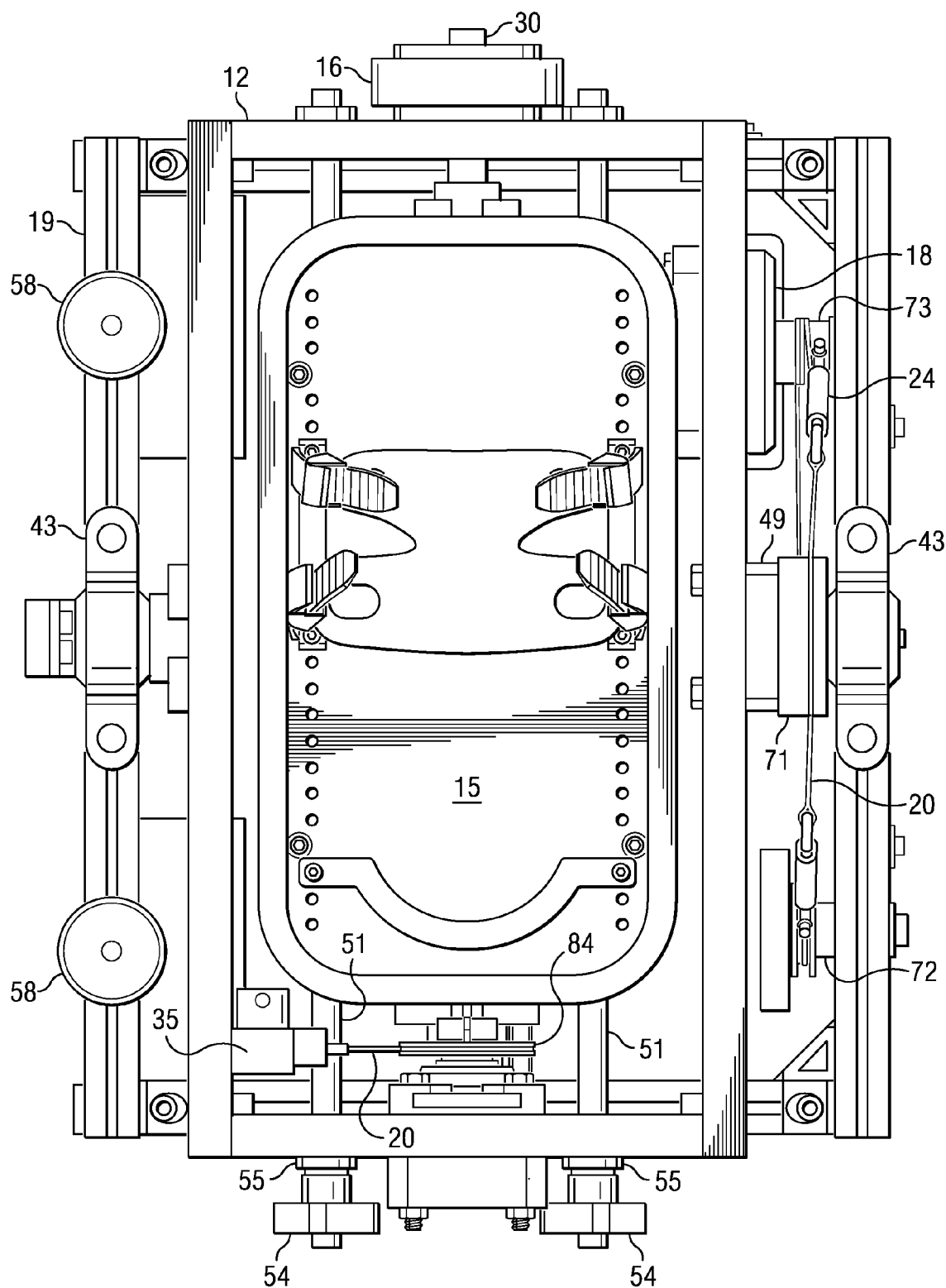
FIG. 1C shows a diagrammatic plan view of a robotic haptic interface in accordance with the present invention.
Figure 1D:
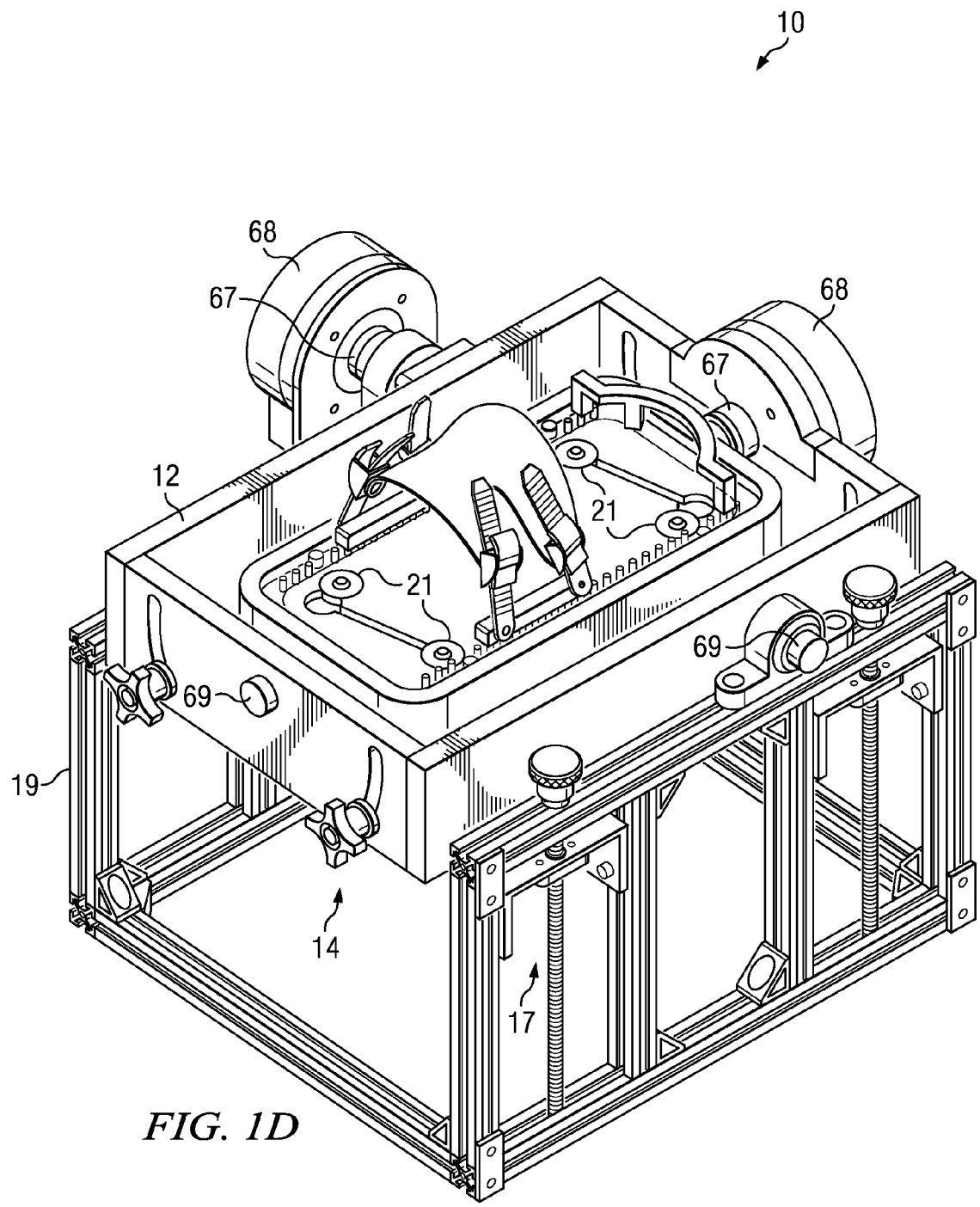
FIG. 1D shows a diagrammatic plan view of a robotic haptic interface with actuators in accordance with the present invention.

Referring to FIG. 1D, a haptic interface 10 having actuators 68 instead of dampers 16, 18 is shown. As previously mentioned, actuators 68, e.g., ERF actuators, are structured and arranged to provide controllable passive resistance as well as active motion for a full robotic capability. Many of the features of the haptic interface 10 having actuators 68 are essentially the same as the haptic interface 10 having dampers 16, 18. However, there is no need for an amplification mechanism 70 and the accelerometer 42 and wire sensor 35 can be replaced by potentiometers 69 to measure joint displacement. Potentiometers are well known to those skilled in the art and will not be discussed further.

The actuators 68 are releasably attached to one end of the shafts 30, 41. Conventionally, torque sensors 67 are provided in combination with the actuators 68, to measure rotation of the shafts 30, 41 and to provide torque data signals to the controller 25. Preferably, the torque sensors 67 are releasably attached to the shafts 30, 41 so as to provide torque signal data about the anterior-posterior axis 11 and the lateral-medial axis 13, respectively. Torque sensors 67 do not have to be attached to the actuators 68 but can be placed serially adjacent to the actuators 68.

In order to provide usable data on motion, force, and so forth, the haptic interface 10 can include a variety of sensing devices ("sensors") or sets of sensors, to generate measurement data for measuring and calculating, inter alia, the angle of movement of the user's ankle, the COP, the user's center of gravity, and so forth. For example, a Polhemus electromagnetic tracker 40 or other sensor that is capable of 6-DOF tracking can be attached to the bottom of the box portion 12 so that the motion/movement of the box portion 12 and the user's ankle which is attached thereto can be monitored in three dimensions (3D). The 3D tracker 40 is adapted to provide positional (x, y, z) and orientation (pitch, roll, yaw) data to a controller 25. For this purpose, the device can include, without limitation, a three-axis magnetic sensor, a three-axis accelerometer in combination with a gyroscope, a three-axis accelerometer in combination with a two-axis magnetic field sensor, and the like. To accommodate the magnetic tracker, the metal parts of the entire device are constructed of non-ferrous material, such as aluminium. This also makes the device lighter in weight and easier to move/relocate the unit in a clinical setting.

The controller 25 processes data from the 6-DOF tracker 40 in combination with software programs, e.g., gaming software, to control the images on a virtual reality (VR) display (not shown). Various VR scenes can make the exercise more enjoyable and interesting, motivating the user to perform the rehabilitation movements.

Referring to FIG. 1C, a second sensor is shown. The second sensor is a cable or wire sensor 22, e.g., a WPS-50 MK30 manufactured by Micro-Epsilon, that is adapted to provide angle position data signals for inversion/eversion rotation of the footplate 15. The wire sensor 22 includes a cable drum 35, which is adapted to provide proportional output data signals of inversion/eversion rotation. More particularly, a pulley 84 is fixedly attached to anterior-posterior shaft 30 and a highly-flexible steel cable 20 is fixedly attached to the pulley 84 and to the cable drum 35. The disposition of the steel cable 20 and cable drum 35 with respect to the pulley 84 transfer rotation into linear movement, which can be provided as output data to the controller 25.

Figure 8:
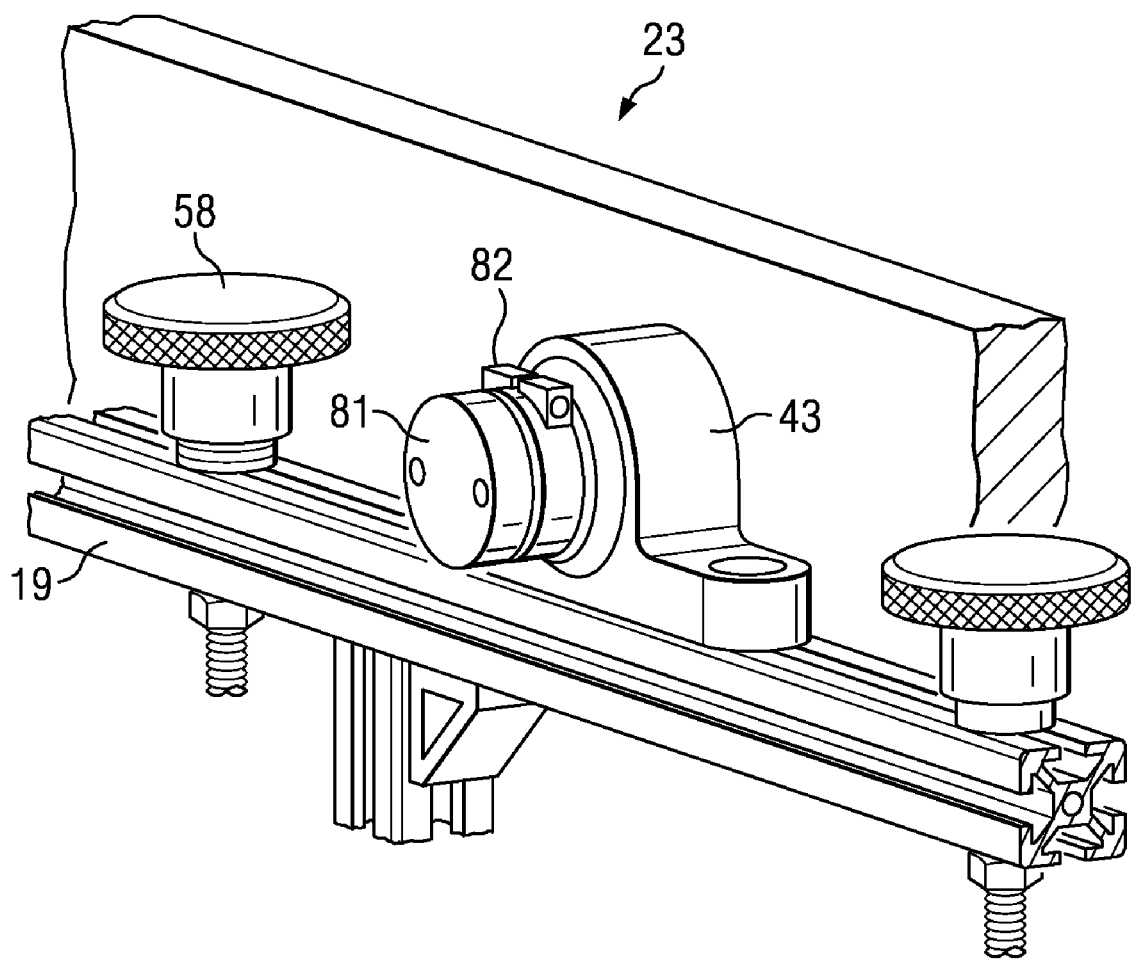
FIG. 8 shows a diagrammatic isometric view of an accelerometer for the haptic interface shown in FIG. 1A and FIG. 1B.

A third sensor is shown in FIG. 8. The sensor is an accelerometer 23, e.g., a DE-ACCM3D Buffered ±3 g Tri-axis accelerometer manufactured by Dimension Engineering of Akron, Ohio, that is adapted to generate angle measurement data signals for determining PF/DF ranges of motion. The accelerometer 23 is structured and arranged to maintain a vertical or substantially vertical orientation when attached to the PF/DF shaft 41 to measure angles directly. The accelerometer 23 can be disposed in a protective housing 81 that can include a clamping device 82 for releasably attaching the housing 81 and accelerometer 23 to the PF/DF shaft 41.

Table I summarizes the dimensions and capabilities of a prototype haptic interface.

TABLE 1

| | |
|---|---|
| Passive Resistance Torque on PF/DF | 0.25-15 Nm |
| Passive Resistance Torque on Inversion/Eversion | 0.25-6 Nm |
| Range of Motion on Plantarflexion | 0-45° |
| Range of Motion on Dorsiflexion | 0-45° |
| Range of Motion on Inversion | 0-12° |
| Range of Motion on Eversion | 0-12° |
| Overall Length | 24.3 in. |
| Overall Width | 16.6 in. |
| Overall Height | 14.6 in. |

Figure 2A:
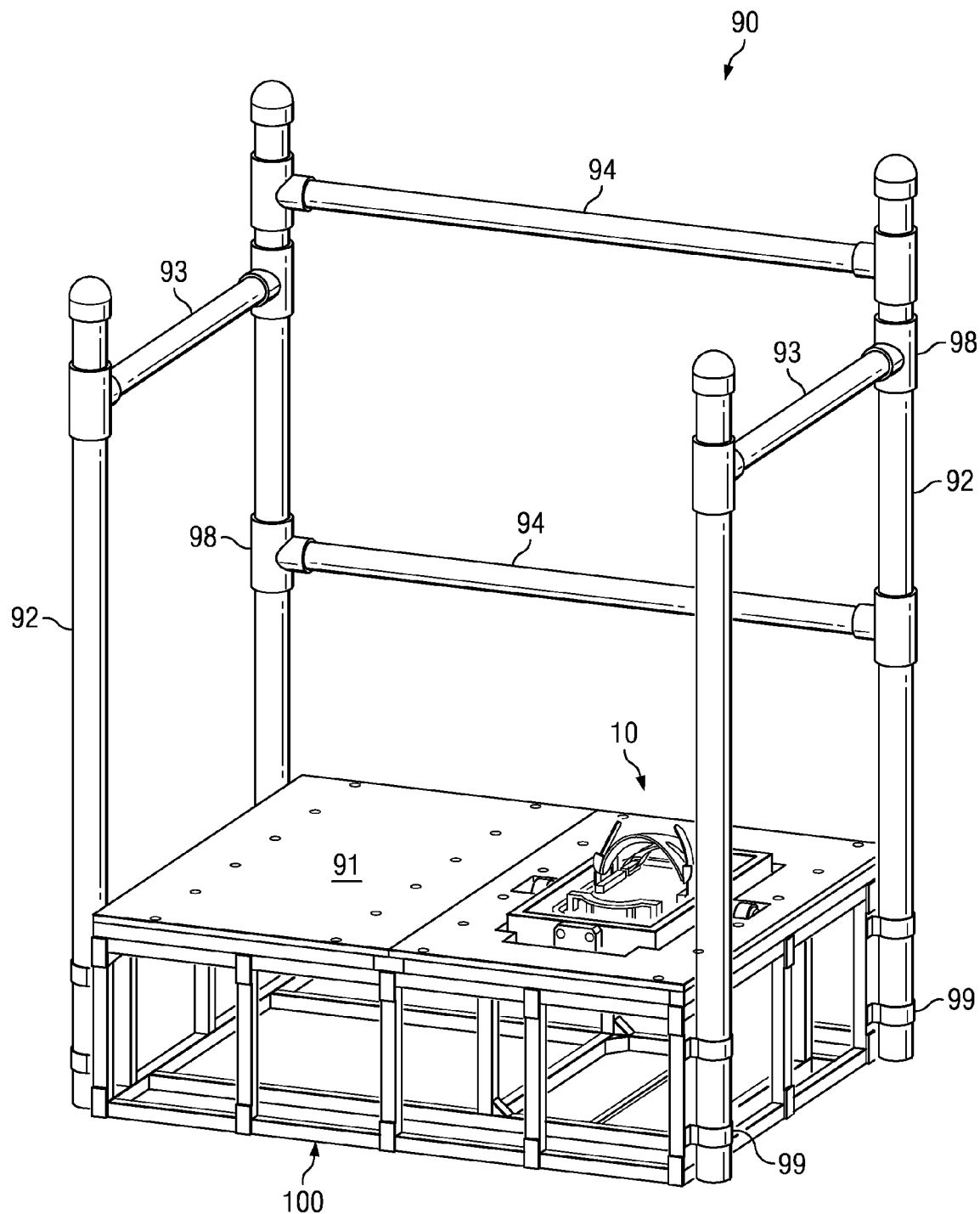
FIG. 2A shows a diagrammatic view of the Northeastern University Virtual Ankle and Balance Trainer (VABAT) rehabilitation system with a single haptic interface in accordance with the present invention.
Figure 2B:
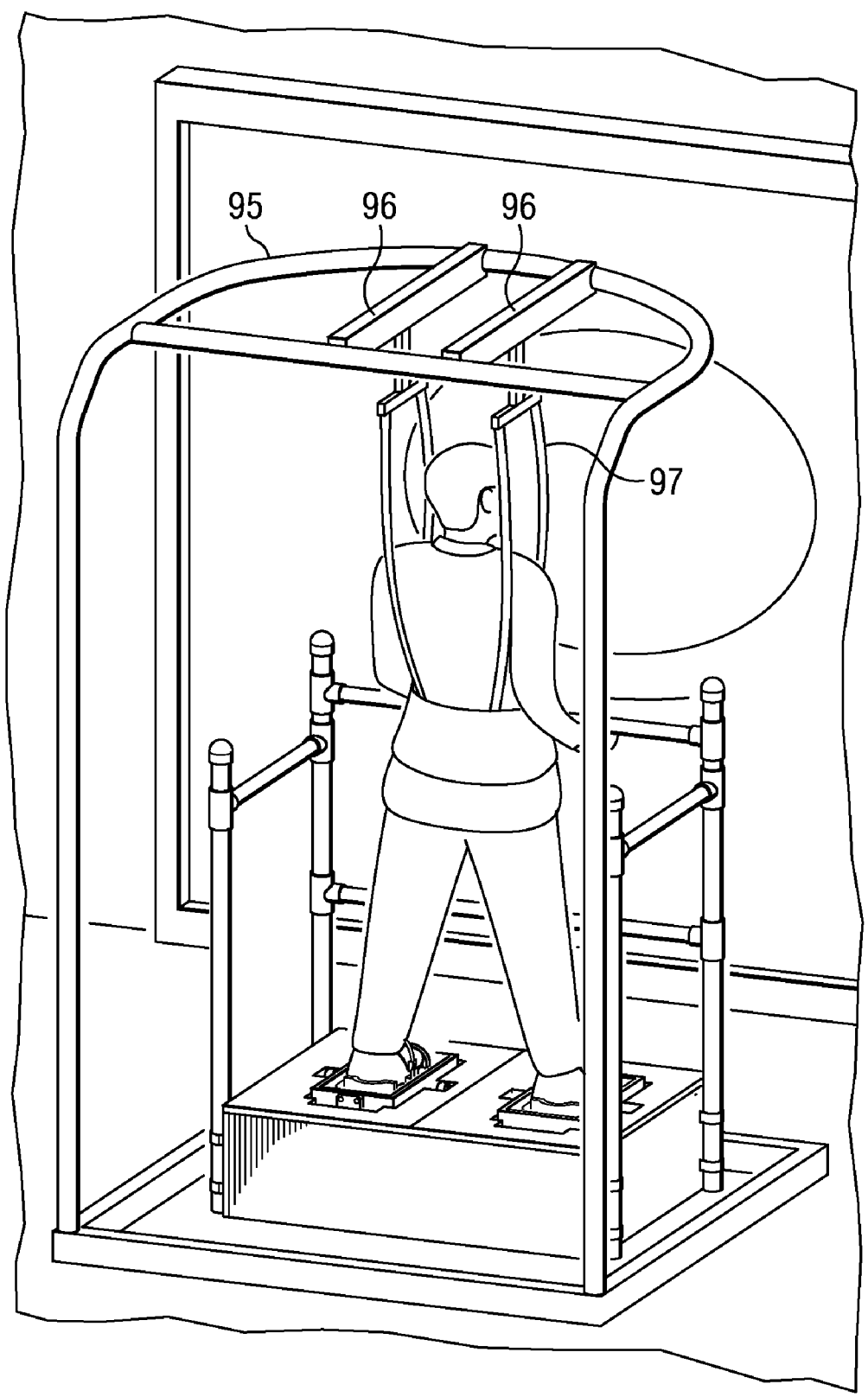
FIG. 2B shows a diagrammatic view of the VABAT rehabilitation system with a two haptic interfaces in accordance with the present invention.
Figure 2C:
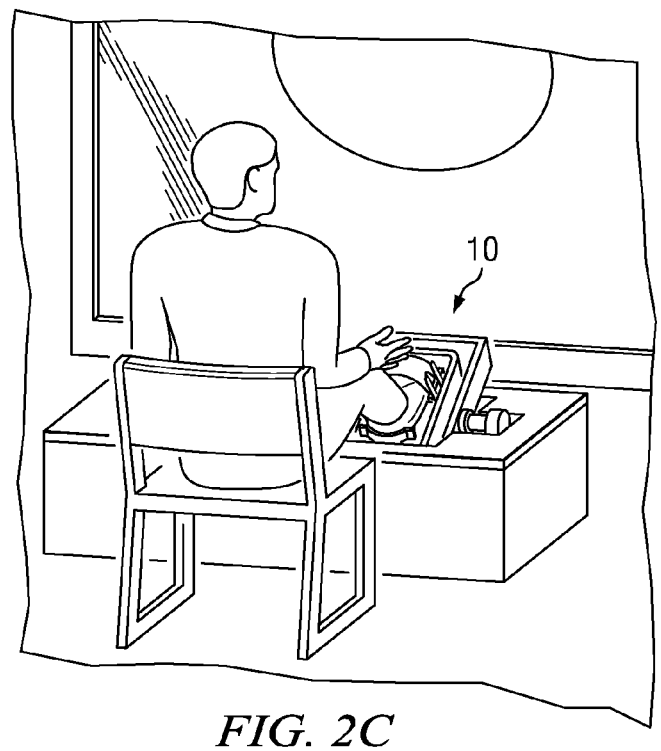
FIG. 2C shows a diagrammatic view of the VABAT of FIG. 2A with a seated user.
Figure 2D:
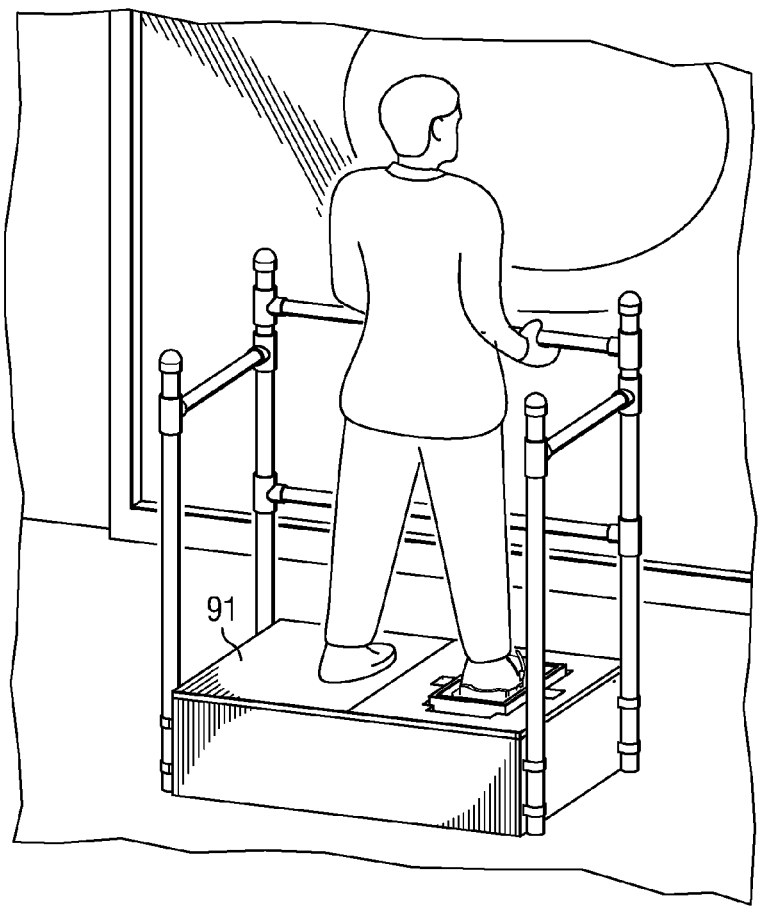
FIG. 2D shows a diagrammatic view of the VABAT of FIG. 2A with a standing user.

When using the haptic interface 10 in the standing mode, it is desirable to support both of the user's feet at the same time and at the same height. Accordingly, supporting platforms 90 that incorporate at least one haptic interface 10 and that enable user's to use the haptic interface 10 in a seated or a standing position are shown in FIGS. 2A-2D. FIG. 2A shows a platform having a single haptic interface 10 for one of the user's feet. FIG. 2B shows a platform 90 having haptic interfaces 10 for both of the user's feet being used in a standing mode. FIG. 2C shows the platform 90 with a single haptic interface 10 being used in a sitting mode. FIG. 2D shows the platform 90 with a single haptic interface 10 being used in a standing mode.

Preferably, the elevation of the footplate 15 and the elevation of the platform floor 91 are the same or substantially the same. Vertical or substantially vertical posts 92 and horizontal or substantially horizontal bars 93, 94 can be provided on opposing sides of the support platform 90 to provide user's with something to hold onto or to lean against during training exercises. Preferably, the height of the horizontal bars 93, 94 is adjustable to accommodate users of different heights. Optionally, the horizontal bars 94 are relocatable to the other side of the supporting platform 90 so that the haptic interface 10 does not have to be moved to exercise Mounting devices 99 can be provided to releasably attach each post 92 to the frame 100 of the support platform 90. Connecting devices 98 can be provided for releasably attaching horizontal bars 93, 94 to posts 92.

When haptic interfaces 10 are provided for both feet (FIG. 2B) for use simultaneously, a supplemental frame 95 can be fixedly attached to the frame 100 and/or to the one or more posts 92. Preferably, the frame 95 is structured and arranged to support a plurality of beams, stringers or joists 96 from which a harness 97 can be hung. Optionally, the harness 97 can be fitted around the user to prevent injury during multiple foot exercises.

As previously mentioned, the haptic interface 10 can be used in a static mode, in which the footplate 15 is locked to prevent movement, or in a dynamic mode, in which the footplate 15 is free to move. With the footplate 15 locked in a flat position, i.e., parallel to the surface 91 of the supporting platform 90, the footplate haptic interface 10 can be used for balance and weight shift training while the user is in the standing position. For more advanced balance training, the footplate 15 can be unlocked, and the user can practice controlled ankle movements, with or without resistance, with one or both ankles. This function is controlled by the robotic interface.

Figure 9:
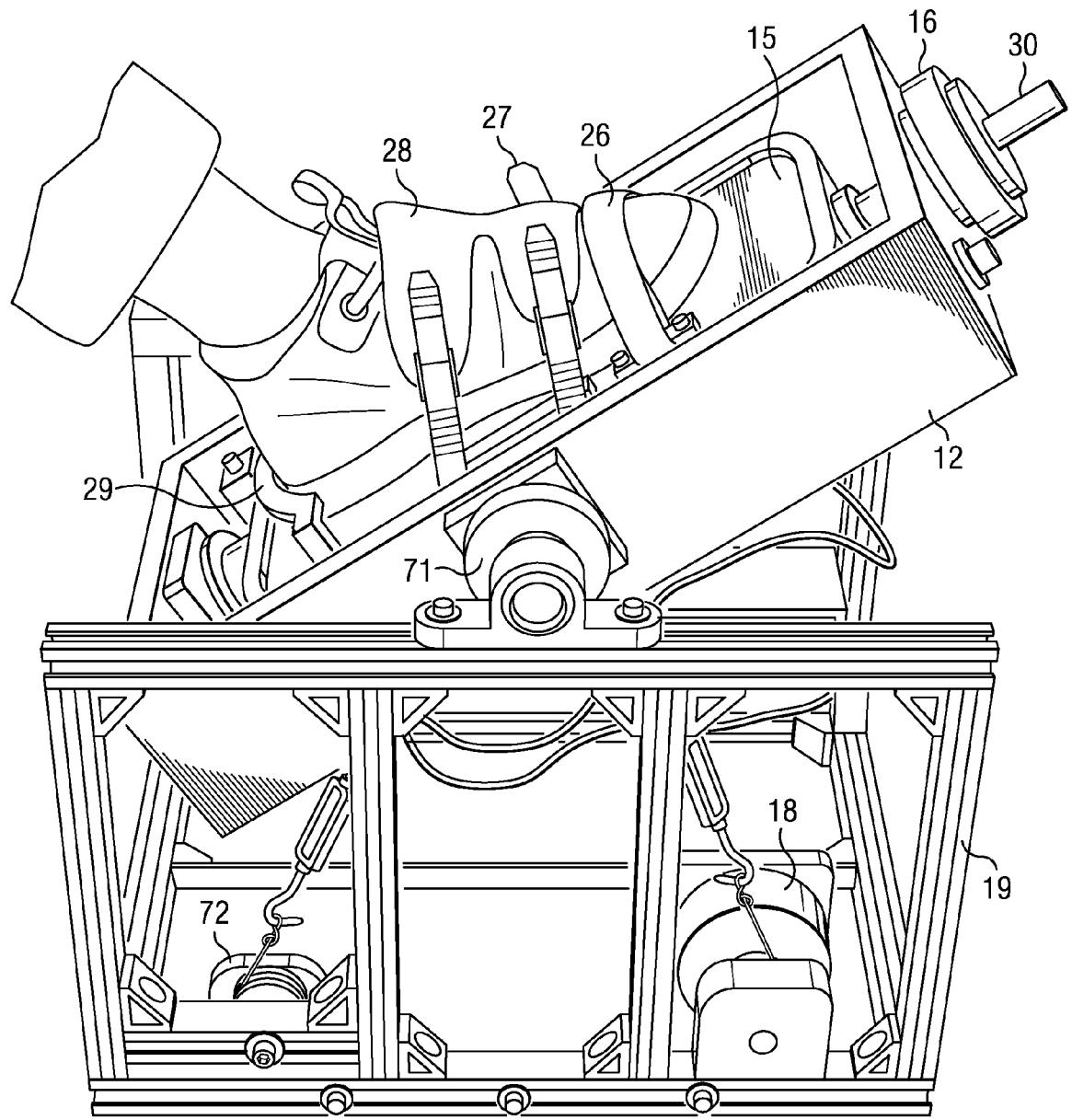
FIG. 9 shows an image of a haptic interface being used in dorsiflexion.

Referring to FIG. 9, for ankle range of motion training, a user places his/her foot or feet on the footplate(s) 15 in either a standing position or a seated position and secures the foot or feet to the footplate 15 using the foot binding straps 27 and 28. For balance training, users stand on the supporting platform 90 and apply force to the footplate(s) 15, attempting to rotate it or to shift their weight to different locations in the standing position.

Figure 10:
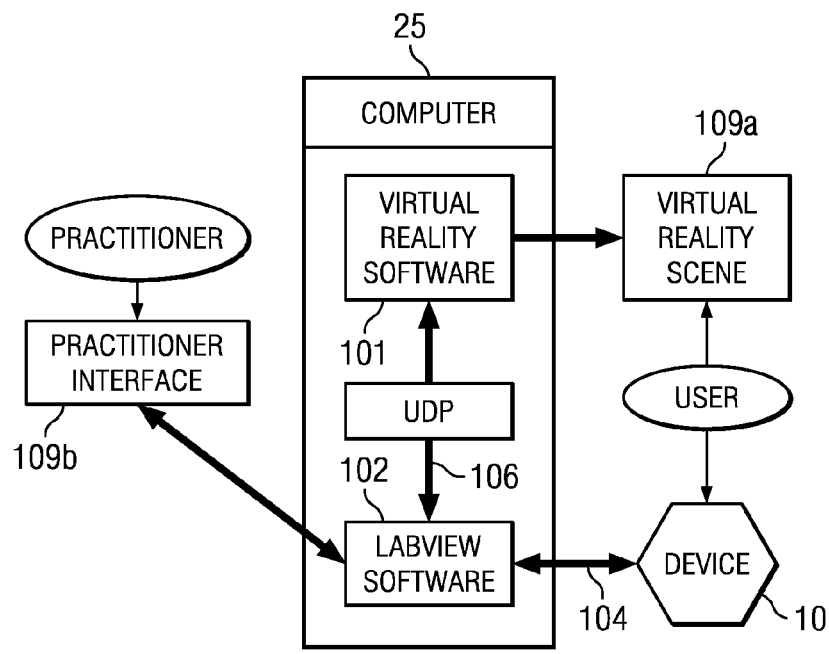
FIG. 10 is a block diagram of the controller system of the present invention.

Referring to FIG. 10, a framework for the controlling system 25 is shown. The controller 25 can include a first processing device 101 and a second processing device 102, which are coupled and adapted to inter-communicate. Those of ordinary skill in the art can appreciate that the functions of the first and second processing devices 101, 102 could be executed on a single processing device. However, for the purpose of this disclosure and for clarity, the processing devices 101, 102 are described as being separate devices.

The first processing device 101 can provide a hosting function and is, further, adapted to communicate with and between at least one of the second processing device 102, a user's graphical display device 109a, and a remote, third-party graphical display device 109b. The latter could be used, e.g., for monitoring a user's performance. The second processing device 102 provides a real-time operating system that is electrically coupled to the robotic haptic interface 10 and that, further, is adapted to receive a myriad of data signals therefrom; to store and/or perform calculations on the received data signals; and to relay or transmit control data signals to the haptic interface 10, viz. the dampers 16, 18 and/or to the graphical display device 109a.

Control hardware is connected to a computer and/or to a gaming console that generate(s) a VR simulation in order to enhance motor learning by engaging users in the therapeutic exercise via interactive gaming. The simulation presents visuo-motor integration tasks to the user as part of the games or scenes and challenges the users with cognitive and problem solving tasks embedded in the games. A variety of performance feedback features can be used in the VR interface to enhance motor learning. A gaming console or gaming engine can be an optional feature of the system. A gaming engine is a software system that is designed for the creation and development of video games.

The control hardware of the rehabilitation system can include a primary, or "host", controller 101 and a secondary, or "real-time target" (RTT), controller 102. The host controller 101 can be a personal computer, e.g., laptop computer, conventional desk top computer, and the like. The real-time target (RTT) controller 102 should be adapted to run a real-time operating system (RTOS).

More particularly, regular data acquisition (DAQ) hardware running on a general-purpose operating system (OS) e.g., Windows® by Microsoft®, cannot guarantee real-time performance since factors, such as programs running in the background, interrupts, and graphical processes, can compromise performance. In contrast, real-time hardware running a real-time operating system (RTOS) allows a programmer to prioritize tasks so that the most critical task always take control of the processor when needed. This property enables reliable applications with predictable timing characteristics.

The primary controller 101 is structured and arranged to store and/or execute (run) the major software programs needed for the system to operate properly. For example, the software can include software for visualization of a game, e.g., Panda 3D, as well as software for providing communication between the primary 101 and the secondary controllers 102, e.g., LabVIEW. Communication between LabVIEW and the Panda 3D engine can be handled using User Datagram Protocol (UDP). Information is transmitted over the network (either on the same computer or via different computers) and then translated in Panda 3D to conform to the movements the user sees as visual feedback. The host controller 101 further includes hardware or software for displaying patient/user and practitioner graphic user interfaces (GUIs), e.g., on display devices 109a and 109b.

The secondary controller 102 is structured and arranged to receive data from and to control the haptic interface 10. To this end, the RTT controller 102 communicates with the haptic interface 10 through a data acquisition card 104. A non-exhaustive list of the various functions performed by the secondary controller 102 includes data acquisition, system control, and so forth. The algorithms, software, driver programs, applications and the like of the haptic interface 10 are run on the real-time platform, i.e., the RTT controller 102, allowing accurate timing characteristics to the interface 10.

The RTT controller 102 further communicates with the host controller 101 to transmit data and critical parameters thereto. Communication between the host controller 101 and the RTT controller 102 is via hardwire or high speed Ethernet 106. Machine code can be developed on the host controller 101, and then deployed to the RTT controller 102. Those of ordinary skill in the art can appreciate that a single controller or more than two controllers may be used. Cost, size, and power requirements, inter alia, will determine an optimal number of controllers.

As previously mentioned, the sensors on the haptic interface 10 provide movement signal data to the host controller 101 via the RTT controller 102. In response to these signal data, the host controller 101 routs commands to the various components of the haptic interface 10 through the RTT controller 102. When operating actively, the host controller 101 can use the haptic interface 10 to force the user to resist applied loads or forces. For example, the strength of the field influencing the ERF or MRF controls the operation of a damper 16, 18. Accordingly, the host controller 101 is adapted to increase/decrease the current from a current power supply to the dampers 16, 18. The current power supply provides the magnetic field that controls the behavior of the MRF or, when actuators are used, provides the electric field that controls the behavior of the ERF.

When operating passively, passive resistance torque during PF/DF and inversion/eversion motions can be adjusted by the therapist, clinician, and/or practitioner using the dampers 16, 18 to suit the user's abilities. Feedback data signals of the forces applied and footplate 15 spatial position and orientation are also transmitted to the controller 25, where these data can be further used and/or can be stored in a user-specific database. Further use of these data can include implementing images, e.g., avatars, icons, and the like, shown on a VR display.

The adaptation of a three-dimensional gaming interface or gaming engine to a rehabilitation system and its advantages are disclosed and described in greater detail in International Patent Application Number PCT/US2010/021483 filed on Jan. 20, 2010, which claims the benefit of U.S. Provisional Patent Application No. 61/145,825 filed on Jan. 20, 2009 and of U.S. Provisional Patent Application No. 61/266,543, filed Dec. 4, 2009—all three of which are incorporated in their entirety herein by reference. As a result, the gaming interface function will not be described in great detail except to describe how the gaming interface interacts with the other components of the system.

Because the extent and nature of a disability may differ from user to user, some users may have problems with inversion/eversion movements, while others may have problems with PF/DF movements. For this reason, a maze design can be created (or selected from existing designs), that allows practitioners, therapists, and the like to focus the therapy on the desired movements of the user's ankles.

For example, with two degrees-of-freedom there are several possibilities for virtual reality scenes. Recalling that there are two training modes: a stable mode, in which the platform is fixed in a stable horizontal position and the user is standing with the involved foot or feet in the haptic interface(s) 10, and a dynamic mode, in which the user can be sitting or standing and the ankle(s) moves freely about either or both axes. For stable-standing, COP measurements and calculations can be used as input to a game interface for weight shifting and balance exercises. For dynamic mode, users can exercise with or without resistance, as determined by the MRF damper settings. The VR software includes a virtual teacher that the user can use to guide the movement, a variety of visual and auditory feedback features, and scoring system to help gauge and measure progress and enhance user motivation during therapy.

Optionally, for standing balance practice, alternative routing modes for the COP game can be provided. Hence, users can select which mode to exercise in: a regular mode or a random mode. Normally, users would use the regular mode to practice and targets would appear in a pre-established sequence. When the random mode is selected, targets would appear in any spot inside the reachable area. Selection can be accomplished, for example, by a mode selection switch (not shown).

Scores can be provided after users finish a game. If the user's score exceeds a pre-established target score, then the user can advance to the next, higher level, which means greater force or rotation requirements. During these exercises, from these data, the therapist, practitioner, clinician, and the like can evaluate which of the user's ankle muscles are the weakest and/or least developed, to determine which exercises are warranted to concentrate on that weaker muscle.

Figure 11:
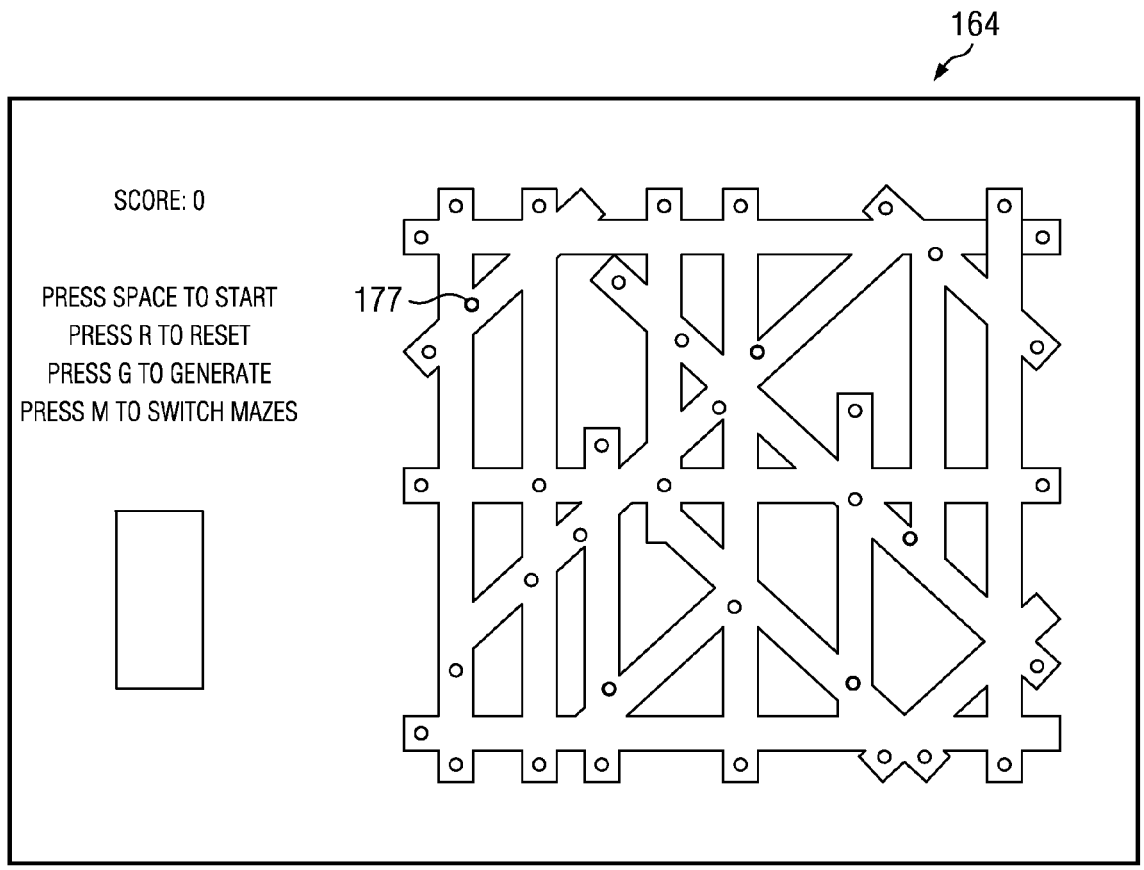
FIG. 11 shows an illustrative maze-type gaming image.
Figure 13:
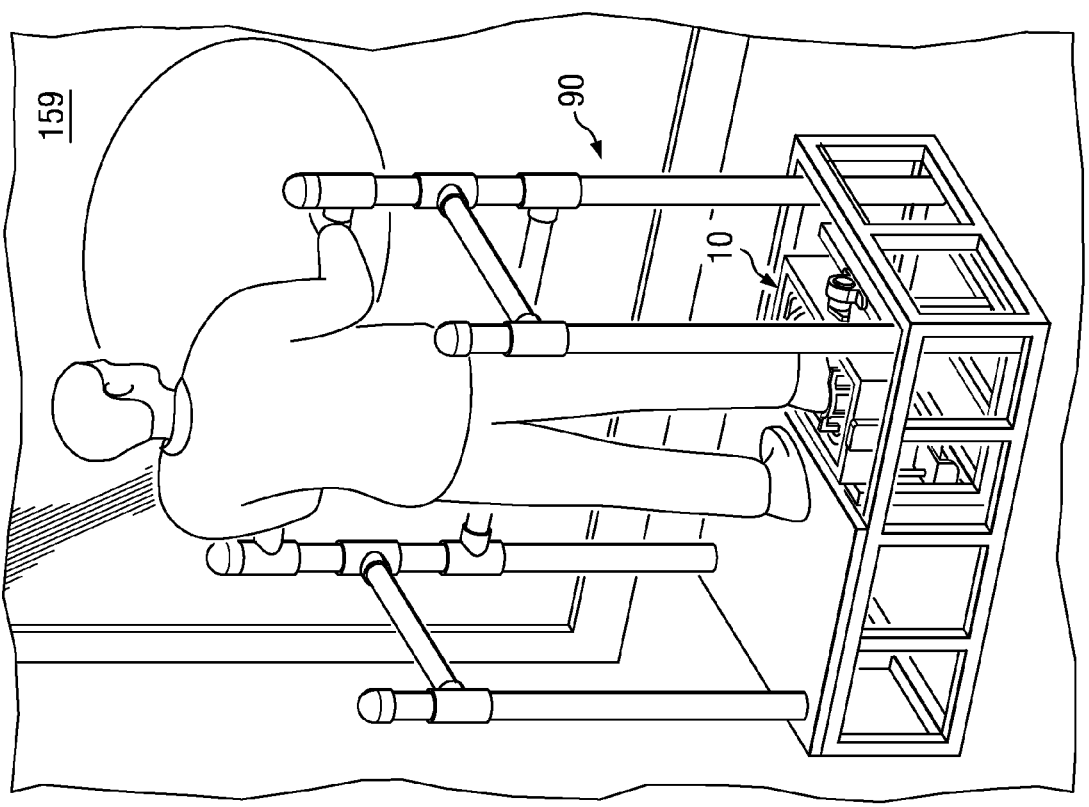
FIG. 13 shows images for sitting and standing users having a large graphical display device.
Figure 13:
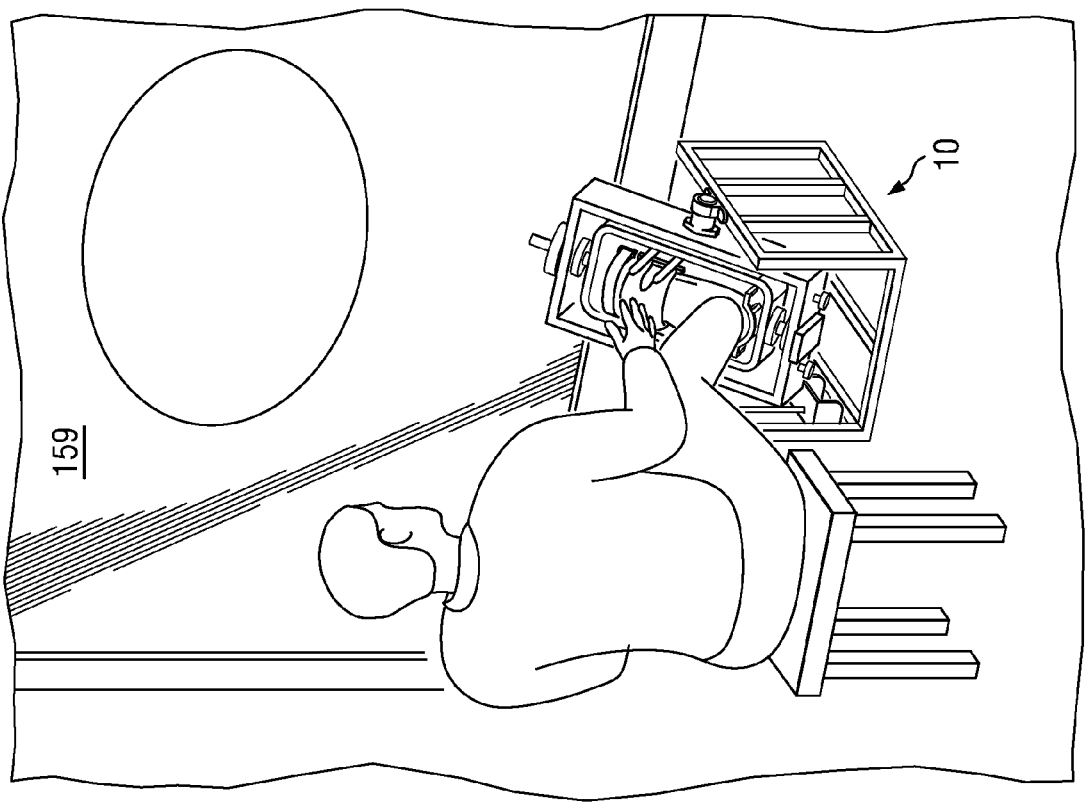

FIG. 11 shows an illustration of an exemplary displayed gaming image 164 that is representative of one of a multiplicity of games or game themes ("scenes") that can be created by a gaming engine and executed (run) by the gaming interface using input data from the 2-DOF robotic haptic interface 10, to drive an icon, cursor, avatar or other figure ("dot" 177) graphically on the screen of the display device 159 (FIG. 13). The illustrative display 164 is a two-dimensional maze, to which a first degree-of-freedom of the robotic haptic interface 10, e.g., PF/DF, is coupled to a first dimension and a second degree-of-freedom, e.g., inversion/eversion, is coupled to a second dimension. More particularly, movement about a first degree-of-freedom controls the x position and movement about a second degree-of-freedom controls the y position in a Cartesian coordinate system. Hence, inversion/eversion motion can result in, i.e., display, movement in a vertical or y-direction, while PF/DF motion can result in, i.e., display, movement in a horizontal or x-direction, or vice versa.

Maze games fall into the category of navigation games, to which can be added obstacle navigation games in which the user avoids virtual objects and triggered event games in which a virtual scene, e.g., a graded slope, forces the user to react to or adapt to an event being displayed. These games can be computer controlled and can use artificial intelligence to react to user input and to force users to react.

A second possible game or scene design uses a first degree-of-freedom to control the direction of the dot 177 and the other degree-of-freedom to control velocity of the dot 177. An example of this design would be to use the PF/DF degree-of-freedom for direction control and the inversion/eversion degree-of-freedom for velocity.

Figure 12:
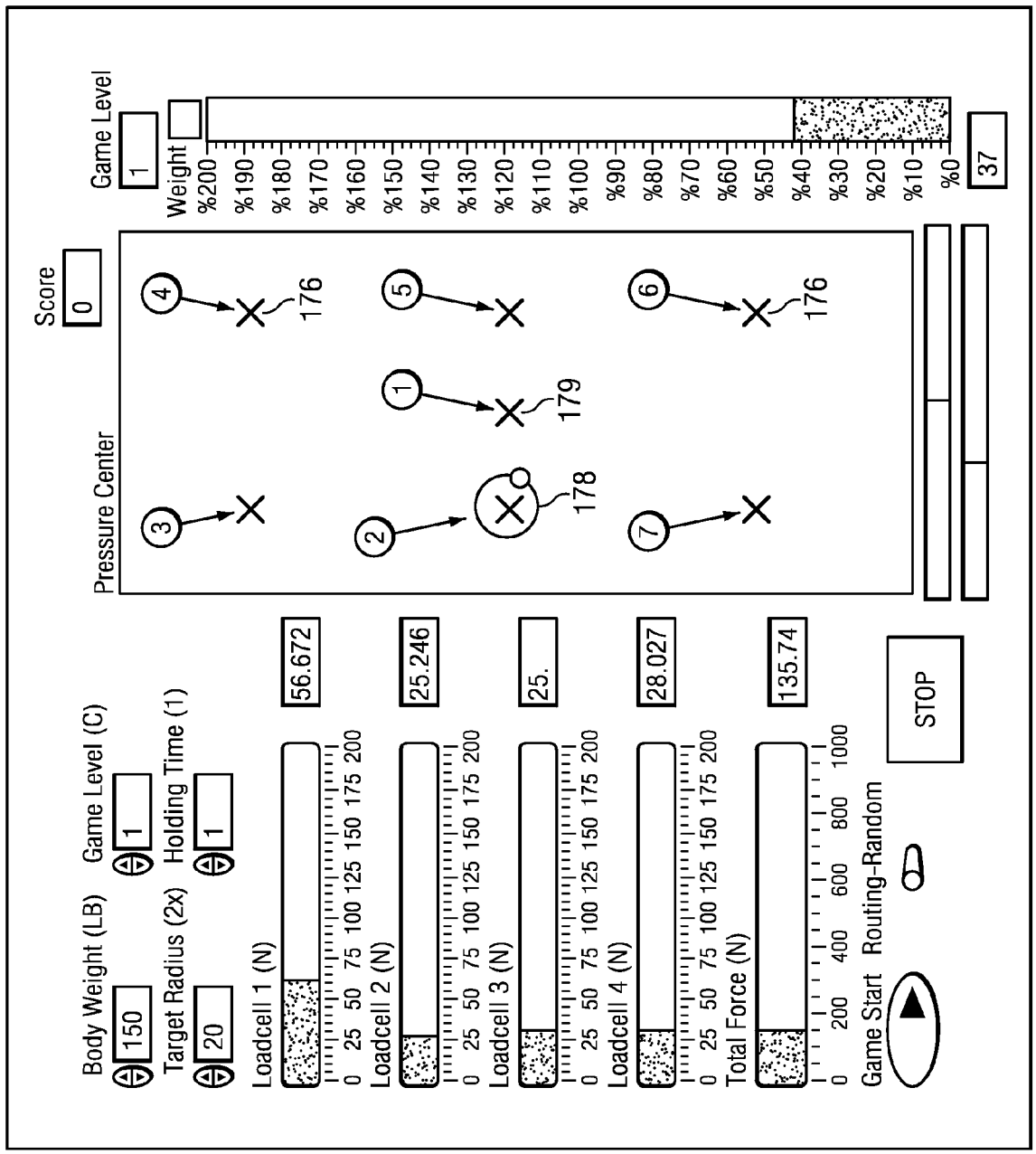
FIG. 12 shows an illustrative center-or-pressure-type gaming image.

A third possible game or scene design is not to use either degree-of-freedom for position, direction, or velocity but instead to control the user's balance on one or both legs using a VR scene. For example, FIG. 12 shows a graphical image for balance control. Six peripheral X's 176 and a single center X 179 are shown. The real-time COP of the user is represented by a relatively large, circular COP icon 178. In order to train the user in balance control, the user must move his/her foot and ankle so that the COP icon 178 is at the center X 179. Other exercises can be used that require the user to move the COP icon 178 to any of the peripheral X's 176.

The graphical user interface (GUI), i.e., the display device 159 (FIG. 13) with a displayed, interactive game scene, provides a visual, interactive gaming environment for performing therapeutic exercises using the robotic haptic interface 10. The GUI provides motivation to the user and real-time feedback, e.g., to the user, a practitioner, a therapist, and the like, concerning the quality of the movements performed by the user, to achieve the motor tasks required to play the games. With such an interface, the user is more motivated to perform visuo-motor tasks that are part of the rehabilitation session in the most appropriate and useful way to achieve motor recovery. Moreover, the practitioner, the therapist, and the like can monitor user performance and progress to evaluate his/her current state and to design future goals for him/her.

With each game, discrete movements of inversion/eversion and PF/DF can be pre-programmed to control certain aspects of a game, such as navigating the dot through a virtual, multiple-dimensional environment. Advantageously, the virtual environment provides challenges, requires the performance of visuo-motor integration tasks (hand-eye coordination), offers real-time visual feedback, and provides input to the controller so that haptic feedback can also be provided. Indeed, a game or a "scene" from a game can be provided in which the controller provides active, haptic feedback, e.g., via the dampers 16, 18, to represent certain virtual events, such as a sloping surface or changing topography.

Knowledge of results and performance are provided continuously as part of the graphical patient interface, to provide the user with a measure of success as well as to encourage the user to do better and more as rehabilitation progresses. For instance, in a goal-oriented game in which the user accumulates points as he/she navigates through a virtual reality environment and/or collects discrete objects, a reward can be provided for achieving a specific score, e.g., point total, during play of the game. For example, the user's score can increase as the user achieves goals in the game and performs tasks that are required, and can decrease when the user does not perform the tasks in accordance with the rules of the game.

Performance data can also be gathered during the game and, in addition to being provided as real-time feedback to the user, can be collected and stored for a later date and/or time for use, for example, by a therapist, clinician, physician, practitioner, and the like, who is skilled in analyzing the data of the therapeutic session, to plan for further rehabilitation sessions. Performance data relate to the characteristics of the movements performed by the subject while accomplishing tasks required by the video games.

The theme and number of potential scenes and games are as limitless as the number of computer games that proliferate in the market today. Basically, a rudimentary virtual reality software scene includes a two-dimensional maze. A velocity model is then applied to the patient/user's position or icon. The scenes can be time-based or goal-based.

Although the multiple degree-of-freedom device has been described as a 2-DOF device, a 3-DOF is also possible by allowing the footplate 15 to rotate in the plane of the footplate 15. Sensing devices such as accelerometers, magnetic field sensing devices, gyroscopes, and the like can be used to measure the change in acceleration and rotational angle of the "yaw" movement.

Furthermore, although the invention has been described in terms of a therapeutic or medical use for medical patients, the device could also be used, for example, in connection with athletic training to strengthen ankle muscles and range of motion and/or in connection with entertainment systems.

Although the invention is described through the above-described exemplary embodiments, it will be understood by those of ordinary skill in the art that modifications to, and variations of, the illustrated embodiments can be made without departing from the inventive concepts disclosed herein. Accordingly, the invention should not be viewed as limited, except by the scope and spirit of the appended claims.

What we claim is:

1. A controllable, selectively-movable, multiple degree-of-freedom, mechatronic ankle and balance trainer device that is releasable attachable to a user's foot, the device comprising:
    a first haptic interface portion that is structured and arranged to rotate about a posterior-anterior axis for providing data on at least one of inversion and eversion rotation of the foot;
    a second haptic interface portion that is structured and arranged to rotate about a lateral-medial axis that is orthogonal or substantially orthogonal to the posterior-anterior axis for providing data on at least one of plantarflexion and dorsiflexion rotation of the foot;
    a first damping or actuating device that is structured and arranged to generate at least one of passive resistance and active force to control rotation about the posterior-anterior axis;
    a second damping or actuating device that is structured and arranged to generate at least one of passive resistance and active force to control rotation about the lateral-medial axis;
    at least one pressure sensing device for measuring force applied to the first haptic interface portion by the foot;
    a sensing device for detecting rotation about the posterior-anterior axis and for generating inversion/eversion rotation data signals;
    a sensing device for detecting rotation about the lateral-medial axis and for generating plantarflexion/dorsiflexion rotation data signals; and
    a controller that is structured and arranged to receive data signals from the sensing devices and to control the at least one of passive resistance and active force of the first and second damping devices.

2. The device as recited in claim 1 further comprising a mechanical stop for controlling a range of rotation about the posterior-anterior axis.

3. The device as recited in claim 2, wherein the mechanical stop includes a pair of adjustable holding blocks, one of the adjustable holding blocks disposed on an anterior side of the lateral-medial axis and the other adjustable holding block disposed on a posterior side of said lateral-medial axis.

4. The device as recited in claim 1 further comprising a mechanical stop for controlling a range of rotation about the lateral-medial axis.

5. The device as recited in claim 4, wherein the mechanical stop includes a pair of selectively-adjustable elongate members that are disposed on an inversion side and an eversion side of and co-axially or substantially co-axially with the posterior-anterior axis.

6. The device as recited in claim 1 further comprising an amplification mechanism for amplifying resistance torque for plantarflexion or dorsiflexion rotation about the lateral-medial axis.

7. The device as recited in claim 6, wherein the amplification mechanism is selected from the group consisting of a cable drive torque amplification mechanism, a piston drive mechanism, a gearbox, and a timing belt mechanism.

8. The device as recited in claim 6, wherein the amplification mechanism includes:
    a first gear that is coupled to a rotating portion of the second damping device;
    a pulley that is coupled to a rotatable shaft mounted to the second haptic interface portion;
    a second gear that is fixedly attached to a supporting structure; and
    cable wire that is routed about the pulley and the first and second gears.

9. The device as recited in claim 1 further comprising a multiple-degree of freedom tracker that is adapted to provide positional and orientation data signals to the controller.

10. A virtual ankle and balance trainer system, the system comprising:
    a stable, stationary supporting platform that is structured and arranged to enable standing and seated exercising;
    at least one controllable, selectively-movable, multiple degree-of-freedom, mechatronic ankle and balance trainer device that is releasably attachable to a user's foot;
    a data acquisition system for receiving data signals from and for transmitting data signals to the ankle and balance trainer device;
    a controller that is structured and arranged to process data signals from sensing devices disposed on the ankle and balance trainer device and to control at least one of passive resistance and active force on said ankle and balance trainer device; and a gaming interface having a graphical display device and adapted to generate virtual reality images using data processed by the controller.

11. The system as recited in claim 10, wherein the system includes an ankle and balance trainer device for each ankle.

12. The system as recited in claim 10, wherein the system is adapted to operate in at least one of: a stable mode in which the ankle and balance trainer device is locked and not capable of movement or rotation; a dynamic mode in which the ankle and balance trainer device is capable of movement or rotation; a standing position, in which a user moves the ankle and balance trainer device while in a standing or substantially standing position; and a sitting position, in which a user moves the ankle and balance trainer device while in a sitting or substantially sitting position.

13. The system as recited in claim 10, wherein the device includes:
a first haptic interface portion that is structured and arranged to rotate about a posterior-anterior axis for providing data on at least one of inversion and eversion rotation of the foot;
a second haptic interface portion that is structured and arranged to rotate about a lateral-medial axis that is orthogonal or substantially orthogonal to the posterior-anterior axis for providing data on at least one of plantarflexion and dorsiflexion rotation of the foot;
a first damping or actuating device that is structured and arranged to generate at least one of passive resistance and active force to control rotation about the posterior-anterior axis;
a second damping or actuating device that is structured and arranged to generate at least one of passive resistance and active force to control rotation about the lateral-medial axis;
at least one pressure sensing device for measuring force applied to the first haptic interface portion by the foot;
a sensing device for detecting rotation about the posterior-anterior axis and for generating inversion/eversion rotation data signals; and
a sensing device for detecting rotation about the lateral-medial axis and for generating plantarflexion/dorsiflexion rotation data signals.

14. The system as recited in claim 13 further comprising a mechanical stop for controlling a range of rotation about the posterior-anterior axis.

15. The system as recited in claim 13 further comprising a mechanical stop for controlling a range of rotation about the lateral-medial axis.

16. The system as recited in claim 13 further comprising an amplification mechanism for amplifying resistance torque for plantarflexion or dorsiflexion rotation about the lateral-medial axis.

17. The system as recited in claim 13 further comprising a multiple-degree of freedom tracker that is adapted to provide positional and orientation data signals to the controller.

18. The system as recited in claim 10 wherein the supporting platform includes a frame for suspending a wearable harness assembly.

19. The system as recited in claim 10 wherein the controller is structured and arranged to generate signals to display real-time images on the display device based on sensing data from the ankle and balance trainer device.

20. The system as recited in claim 10 wherein the controller is structured and arranged to provide haptic feedback to the ankle and balance trainer device as a function of gaming software and images shown on the display device.

21. The system as recited in claim 13, wherein the controller is adapted to use inversion/eversion rotation data signals and plantarflexion/dorsiflexion rotation data signals to control at least one of a position, a direction of movement, and a velocity of movement of an avatar shown in an image on the display device.

22. The system as recited in claim 13, wherein the controller is adapted to collect and store the data.

* * * * *